(12) United States Patent
Clendennen et al.

(10) Patent No.: US 10,961,180 B2
(45) Date of Patent: Mar. 30, 2021

(54) BRANCHED TRIALKYL AMINE OXIDES

(71) Applicant: Eastman Chemical Company, Kingsport, TN (US)

(72) Inventors: Stephanie Kay Clendennen, Kingsport, TN (US); Vasudev R. Bhonde, Johnson City, TN (US); Damon Ray Billodeaux, Longview, TX (US); Matthew Allen Boone, Kingsport, TN (US); Kim Dumoleijn, Eede (NL); Stijn Simonne Paul Van de Vyver, Ghent (BE); Kristof Moonen, Hamme (BE); Neil Warren Boaz, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 27 days.

(21) Appl. No.: 16/243,232

(22) Filed: Jan. 9, 2019

(65) Prior Publication Data

US 2019/0218169 A1    Jul. 18, 2019

Related U.S. Application Data

(60) Provisional application No. 62/616,502, filed on Jan. 12, 2018.

(51) Int. Cl.
| | |
|---|---|
| *C09K 8/584* | (2006.01) |
| *C07C 207/02* | (2006.01) |
| *C07C 201/00* | (2006.01) |
| *C11D 1/75* | (2006.01) |
| *C11D 1/83* | (2006.01) |

(Continued)

(52) U.S. Cl.
CPC ............ *C07C 207/02* (2013.01); *A01N 33/12* (2013.01); *A01N 37/44* (2013.01); *A01N 41/08* (2013.01); *A61K 8/416* (2013.01); *A61K 8/44* (2013.01); *A61K 8/466* (2013.01); *A61Q 5/02* (2013.01); *A61Q 19/10* (2013.01); *B01J 31/0239* (2013.01); *C07C 45/62* (2013.01); *C07C 45/72* (2013.01); *C07C 45/74* (2013.01); *C07C 201/00* (2013.01); *C07C 209/22* (2013.01); *C07C 211/04* (2013.01); *C07C 211/08* (2013.01); *C07C 211/63* (2013.01); *C07C 211/64* (2013.01); *C07C 215/10* (2013.01); *C07C 229/12* (2013.01); *C07C 291/04* (2013.01); *C07C 309/14* (2013.01); *C07C 311/32* (2013.01); *C07H 5/06* (2013.01); *C09D 7/63* (2018.01); *C09K 8/524* (2013.01); *C09K 8/584* (2013.01); *C10L 1/18* (2013.01); *C11D 1/75* (2013.01); *C11D 1/83* (2013.01); *C11D 1/835* (2013.01); *C11D 1/90* (2013.01); *C11D 1/94* (2013.01); *C11D 3/395* (2013.01); *C11D 3/3942* (2013.01); *C11D 3/43* (2013.01);

(Continued)

(58) Field of Classification Search
CPC ..... C07C 207/02; C07C 45/72; C07C 209/22; C07C 211/63; C07C 211/64; C07C 201/00; C07C 2601/16; C07C 311/32; C07C 211/08; C07C 291/04; C07C 45/74; C07C 215/10; C07C 45/62; C07C 211/04; C07C 229/12; C07C 309/14; A61K 8/416; A61K 8/44; A61K 8/466; A61Q 5/02; A61Q 19/10; C11D 1/90; C11D 1/75; C11D 1/83; C11D 1/835; C11D 1/94; C11D 3/3942; C11D 11/0023; C11D 11/0017; C11D 3/43; C11D 3/395; A01N 41/08; A01N 33/12; A01N 37/44; B01J 31/0239; C07H 5/06; C10L 1/18; C09D 7/63; C09K 8/584; C09K 8/524
See application file for complete search history.

(56) References Cited

U.S. PATENT DOCUMENTS 3,336,387 A * 8/1967 Finch .................... C07C 291/04
564/297
4,207,260 A    6/1980 Imai
(Continued)

FOREIGN PATENT DOCUMENTS

| CN | 107028838 A | 8/2017 |
|---|---|---|
| JP | 48039451 A | 6/1973 |

(Continued)

OTHER PUBLICATIONS

Laundary Stain Remover datasheet downloaded on Jun. 4, 2020.*
(Continued)

*Primary Examiner* — Kumar R Bhushan
(74) *Attorney, Agent, or Firm* — Kenrick L. Vidale

(57) ABSTRACT

The invention provides branched trialkylamine oxides with improved properties. The trialkylamine oxides of the invention produced from branched trialkylamines, in one embodiment, can be made using certain branched C10-12 enals and aldehydes. The invention also provides an trialkylamine oxide having the formula:

wherein R5, R6 and R7 are independently at least one of C3H7, C2H5, CH3, or H, or mixtures thereof; and wherein R5 and R6 are not H at the same time. In one embodiment, the trialkylamine oxides of the invention can be useful in making various products, for example, as surfactants.

14 Claims, No Drawings

(51) Int. Cl.

| | | |
|---|---|---|
| C11D 1/835 | (2006.01) | |
| C11D 1/94 | (2006.01) | |
| C10L 1/18 | (2006.01) | |
| C11D 3/39 | (2006.01) | |
| C11D 11/00 | (2006.01) | |
| C11D 3/43 | (2006.01) | |
| C09D 7/63 | (2018.01) | |
| C11D 3/395 | (2006.01) | |
| A01N 41/08 | (2006.01) | |
| C07C 311/32 | (2006.01) | |
| C07C 211/08 | (2006.01) | |
| C09K 8/524 | (2006.01) | |
| A01N 37/44 | (2006.01) | |
| C07C 291/04 | (2006.01) | |
| C07C 45/74 | (2006.01) | |
| C07C 215/10 | (2006.01) | |
| C07C 45/62 | (2006.01) | |
| A61K 8/41 | (2006.01) | |
| A61K 8/44 | (2006.01) | |
| A61K 8/46 | (2006.01) | |
| A61Q 5/02 | (2006.01) | |
| A61Q 19/10 | (2006.01) | |
| C07C 211/04 | (2006.01) | |
| C07C 229/12 | (2006.01) | |
| C07C 309/14 | (2006.01) | |
| C07H 5/06 | (2006.01) | |
| C11D 1/90 | (2006.01) | |
| A01N 33/12 | (2006.01) | |
| B01J 31/02 | (2006.01) | |
| C07C 45/72 | (2006.01) | |
| C07C 209/22 | (2006.01) | |
| C07C 211/63 | (2006.01) | |
| C07C 211/64 | (2006.01) | |

(52) U.S. Cl.
CPC ...... *C11D 11/0017* (2013.01); *C11D 11/0023* (2013.01); *C07C 2601/16* (2017.05)

(56) References Cited

U.S. PATENT DOCUMENTS

| | | | |
|---|---|---|---|
| 4,276,205 A | 6/1981 | Ferry | |
| 4,292,242 A | 9/1981 | Laine | |
| 4,404,404 A | 9/1983 | Swift et al. | |
| 4,426,542 A | 1/1984 | Barker et al. | |
| 4,465,843 A | 8/1984 | del Valle | |
| 4,598,162 A | 7/1986 | Forster et al. | |
| 4,994,622 A | 2/1991 | Fong et al. | |
| 5,001,284 A | 3/1991 | Dupont et al. | |
| 5,030,774 A | 7/1991 | Oswald et al. | |
| 5,266,730 A | 11/1993 | Abe et al. | |
| 5,371,250 A | 12/1994 | Seitz et al. | |
| 5,491,240 A | 2/1996 | Arnold et al. | |
| 5,955,633 A * | 9/1999 | Prabhu | C07C 291/04 564/298 |
| 6,037,497 A | 3/2000 | Thomas et al. | |
| 6,090,986 A | 7/2000 | Godwin et al. | |
| 7,049,270 B2 | 5/2006 | Lennon et al. | |
| 10,640,452 B2 | 5/2020 | Clendennen et al. | |
| 2004/0138510 A1 | 7/2004 | Kramarz et al. | |
| 2008/0167499 A1 | 7/2008 | Molitor et al. | |
| 2012/0157365 A1 | 6/2012 | Fevola | |

FOREIGN PATENT DOCUMENTS

| | | |
|---|---|---|
| JP | H02160757 A | 6/1990 |
| JP | H11279133 A | 10/1999 |
| JP | 2014118385 A | 6/2014 |
| WO | WO 85/02173 A1 | 5/1985 |
| WO | WO 2003/091197 A1 | 11/2003 |

OTHER PUBLICATIONS

Office Action dated Jun. 26, 2019 received in co-pending U.S. Appl. No. 16/243,237.

Tolgyesi et al.; "Mothproofing with ammonium quats;" Chem Tech; Jan. 1971; pp. 27-30.

Notice of Allowance dated Jan. 14, 2020 received in co-pending U.S. Appl. No. 16/243,237.

Notification of Transmittal of the International Search Report and the Written Opinion of the International Searching dated May 14, 2019 received in International Application No. PCT/US2019/012976.

Co-pending U.S. Appl. No. 16/243,229, filed Jan. 9, 2019; Clendennen et al.

Co-pending U.S. Appl. No. 16/243,237, filed Jan. 9, 2019; Clendennen et al.

Mills et al.; "Physical and Thermodynamic Properties for Novel $C_{14}$ Unsaturated Aldehydes and $C_{16}$ Saturated Amines;" J. Chem. Eng. Data; 1987; 32; pp. 251-265.

Fassbach et al.; "Renewable Surfactants through the Hydroaminomethylation of Terpenes;" ChemCatChem; 2017; 9; pp. 1359-1362.

Gomez et al.; "The Reductive Amination of Aldehydes and Ketones and the Hydrogenation of Nitriles: Mechanistic Aspects and Selectivity Control;" Adv. Synth. Catal.; 2002; 344; pp. 1037-1057.

Varjosaari et al.; "Simple Metal-Free Direct Reductive Amination Using Hydrosilatrane to Form Secondary and Tertiary Amines;" Adv. Synth. Catal.; 2017; 359; pp. 1872-1878.

Liang et al.; "Au/$TiO_2$ catalyzed reductive amination of aldehydes and ketones using formic acid as reductant;" Org. Chem. Front.; 2016; 3; pp. 505-509.

ASTM D2281-68; Standard Test Method for Evaluation of Wetting Agents by the Skein Test.

ASTM 4265; Standard Guide for Evaluating Stain Removal Performance in Home Laundering.

ASTM-E2407; Standard Test Method for Effectiveness of Defoaming Agents.

Moore et al.; "Role of the Surfactant Polar Head Structure in Protein—Surfactant Complexation: Zein Protein Solubilization by SDS and by SDS/$C_{12}E_n$ Surfactant Solutions;" Langmuir; 2003; 19; pp. 1009-1016.

Office Action dated Apr. 13, 2020 received in co-pending U.S. Appl. No. 16/243,229.

* cited by examiner

BRANCHED TRIALKYL AMINE OXIDES

CROSS REFERENCE TO RELATED APPLICATIONS

This application claims priority under 35 U.S.C. 119(e) to U.S. Provisional Application Ser. No. 62/616,502 filed Jan. 12, 2018, which is incorporated herein by reference in its entirety.

FIELD OF THE INVENTION

The invention generally relates to the field of organic chemistry. It also relates to branched trialkyl amine oxides, products made therefrom, and methods of manufacturing them. It further relates to novel branched trialkyl amine oxides which are useful as surfactants.

BACKGROUND OF THE INVENTION

There is a commercial need for novel surfactants with desirable properties such as low foaming, effective oily soil removal, performance in cold water, compatibility with other ingredients in a cleaning formula, mildness to skin, and a favorable environmental and safety profile.

A common trialkylamine hydrophobe used to make surfactants is dimethyl alkyl amine, made from C12 and C14 fatty alcohols reacted with dimethylamine, sometimes referred to as dimethyl laurylamine, or DIMLA. Neither DIMLA, its trialkylamine intermediate or the surfactants made from it contain branching.

Certain petrochemical detergent alcohols can also be used as surfactant hydrophobes. The most common synthetic detergent alcohols are produced by ethylene oligomerization, for instance, according to the Shell Higher Olefin Process (SHOP) process or the Ziegler alcohol process. Olefins can also be obtained from a Fischer-Tropsch process out of synthesis gas. The processing of producing detergent alcohols adds considerably to energy and facilities usage and consequently to product cost. Also, the resulting hydrophobes are typically over 85% linear.

Certain mixtures of C14 branched hydrophobes have also been described with some of the hydrophobe mixture containing a single branch point. When mixtures of hydrophobes are used to make surfactants, the individual hydrophobes in the mixture are not known to perform as well as the mixtures.

There remains a need in the industry for novel compositions which can be used to produce novel surfactants with desirable properties, for example, low foaming, mildness to skin, effective oily soil and/or stain removal (especially in cold water), high solubility in water, no gelling, ease of formulation, compatibilization or stabilization of other ingredients in a formula, retention of good hydrophobicity compared to linear hydrophobes, tolerance of extreme pH, and/or a favorable environmental and safety profile. There also remains a need in the industry for effective reactants and processes to make branched surfactants and corresponding surfactant intermediates with fewer reaction byproducts, fewer reaction steps, and/or reduced reaction solvent(s).

SUMMARY OF THE INVENTION

In view of the above commercial shortcomings in the art, the present disclosure addresses the need for novel compositions, e.g., surfactants, with one or more of the following desirable properties: (1) low foaming, such as according to ASTM E2407, (2) mildness to skin, such as predicted by a zein solublization test or patch test, (3) effective oily soil and/or stain removal, especially in cold water, such as according to ASTM 4265, (4) compatibility with other ingredients in a cleaning formula, and (5) a favorable environmental profile, (6) high solubility in water; (7) no gelling, (8) ease of formulation, and (9) compatibilization or stabilization of other ingredients in a formula, (10) retains good hydrophobicity compared to linear hydrophobes, (11) tolerance of extreme pH, (12) antimicrobial activity, (13) biodegradability, such as according to OECD 301B and/or (14) an improved safety profile. The compositions of this invention can provide desirable properties for a variety of applications.

The invention is as set forth in the Field of the Invention, the Summary of the Invention, the Description, the Examples, the appended Claims, and the Abstract.

For the ease of reference but not intending to be limiting in any way, certain aspects of this disclosure are numbered consecutively, as follows:

In aspect 1, this invention provides at least one trialkylamine oxide having the formula:

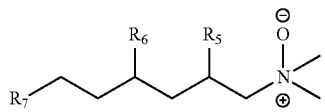

wherein R5, R6 and R7 are independently at least one of C3H7, C2H5, CH3, or H, or mixtures thereof; and wherein R5 and R6 are not H at the same time.

In aspect 2, this invention provides at least one trialkylamine oxide of aspect 1 having the formula:

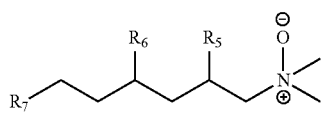

wherein R5 and R6 are C3H7, C2H5, CH3, or mixtures thereof; and
wherein R7 is one of C3H7, C2H5, CH3, H or combinations thereof.

In aspect 3, this invention provides at least one trialkylamine oxide of any one of aspects 1 or 2 wherein R6 is CH3 or C2H5.

In aspect 4, this invention provides at least one trialkylamine oxide of aspect 3 wherein R5 and R6 independently are C2H5.

In aspect 5, this invention provides at least one trialkylamine oxide of aspect 4 which is 2,4-diethyl-N,N-dimethyloctan-1-amine oxide.

In aspect 6, this invention provides at least one trialkylamine oxide of any one of aspects 1-3 wherein R5 is CH3 or C2H5.

In aspect 7, this invention provides at least one trialkylamine oxide of aspect 6 wherein R5 is CH3 and R6 is C2H5.

In aspect 8, this invention provides at least one trialkylamine oxide of aspect 7 which is 4-ethyl-N,N-2-trimethyloctan-1-amine oxide.

In aspect 9, this invention provides at least one trialkylamine oxide of any one of aspect 1-8 wherein foaming does not persist for more than 5 minutes when tested according to modified ASTM Method E2407, wherein the method modification is to substitute at least one of said trialkylamine oxides for sodium lauryl ether sulfate and to use no defoamer.

In aspect 10, this invention provides at least one trialkylamine oxide of any one of aspects 1-9 having a Zein score of less than 1.0 when normalized to linear alcohol ethoxylate (LAE 10) using the Zein Solubilization Test.

In aspect 11, the invention provides at least one trialkylamine oxide of any one of aspects 1-10 having a Zein score of less than 0.50, or less than 0.40, or less than 0.30, or less than 0.20, or less than 0.10, or less than 0.05, or less than 0.02 when normalized to linear alcohol ethoxylate (LAE 10) using the Zein Solubilization Test.

In aspect 12, the invention provides at least one trialkylamine oxide of any one of aspects 1-11 comprising 0.05 weight % of amine oxide in (1500 ml) deionized water which has a Draves wet-out time (WOT) in seconds of greater than 33 seconds according to Draves Wetting Test or ASTM Method D2281-68.

In aspect 13, the invention provides at least one trialkylamine oxide of aspect 12 having a Draves wet-out time (WOT) in seconds of greater than 300 seconds according to Draves Wetting Test or ASTM D2281-68.

In aspect 14, this invention provides a composition comprising at least one trialkylamine oxide of any one of aspects 1-13.

In aspect 15, this invention provides a composition comprising at least one trialkylamine oxide of any one of aspects 1-14 wherein amines oxides other than those of any one of aspects 1-14 are excluded from the composition.

In aspect 16, this invention provides the composition of any one of aspects 14 or 15 comprising at least one nonionic surfactant, anionic surfactant, cationic surfactant, amphoteric surfactant, or combinations thereof.

In aspect 17, this invention provides the composition of any one of aspects 14-16 comprising 0.01% to 30% by weight of the trialkylamine oxide or a combination of the amine oxides, based on the total weight of the composition equaling 100 weight %.

In aspect 18, the invention provides a composition selected from any one of aspects 14-17 wherein the trialkylamine(s) used to make the trialkylamine oxide(s) does not contain any isomeric compound or mixtures, wherein said mixtures can contain a number of isomeric compounds, and wherein said isomeric compound(s) can be selected from those of structures:

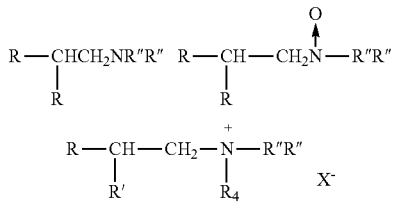

having from 10 to 18 carbon atoms in the R(R')CHCH2- moiety in which R has 5 to 9 carbon atoms, and R' has from 3 to 7 carbon atoms, with most of the compounds having additional methyl or ethyl branches, and in which R" and R'" are alkyl or hydroxyalkyl groups or hydrogen and X– is an anion.

In aspect 19, the invention provides a composition of any one of aspects 14-18 wherein the trialkylamine(s) used to make the trialkylamine oxide(s) does not contain any isomeric compound or mixture of isomers of aspect 18, wherein said mixtures can contain a number of isomeric compounds, wherein said isomeric compound(s) can be selected from tertiary amines with a higher branched-chain alkyl substituent characterized as having 10 to 18 carbon atoms and an alkyl branch at the 2-position containing 3 to 7 carbon atoms, and additional branching in most of the isomers, with most of the additional branches being methyl groups.

In aspect 20, the invention provides a composition selected from any one of aspects 14-19 wherein the trialkylamine(s) used to make the trialkylamine oxide(s) of the invention do not contain any isomers or mixtures of isomers of any one of aspects 18 or 19 wherein said mixtures contain a number of isomeric compounds, and wherein said isomeric compounds can be selected from tertiary amines with a higher branched-chain alkyl substituent characterized as having 12 carbon atoms and an alkyl branch at the 2-position containing 5 carbon atoms or greater, whether or not with additional branching in most of the isomers, whether or not with most of the additional branches are methyl groups and/or ethyl groups.

In aspect 21, the invention provides a composition comprising at least one trialkylamine oxide selected from any one of aspects 1-13 but which does not contain any trialkylamine oxides or mixtures of amine oxides other than those described herein as being within the scope of this invention.

In aspect 22, this invention provides the composition of any one of aspects 14-21 comprising at least one bleach compound, hydrogen peroxide compound, or combinations thereof.

In aspect 23, this invention provides the composition of any one of aspects 14-22 comprising 1.4 weight % of the trialkylamine oxide of any one of aspects 1-13 further comprising 2.5 weight % NaCl, 4.3 weight % sodium lauryl sulfate, 4.3 weight % sodium lauryl ether sulfate in deionized water wherein said composition has a Brookfield viscosity of less than 4000 centipoise at a shear rate of 3/s.

In aspect 24, this invention provides the composition of aspect 23 comprising 3.0 weight percent by volume of NaCl in deionized water wherein said composition has a Brookfield viscosity of less than 3500 centipoise at a shear rate of 3/s.

In aspect 25, this invention provides the composition of aspect 24 comprising 3.5 weight percent by volume of NaCl in deionized water wherein said composition has a Brookfield viscosity of less than 2100 centipoise at a shear rate of 3/s.

In aspect 26, this invention provides the composition of aspect 25 comprising 4.0 weight percent by volume of NaCl in deionized water wherein said composition has a Brookfield viscosity of less than 1500 or less than 1000 or less than 700 centipoise at a shear rate of 3/s.

In aspect 27, this invention provides home care products, industrial cleaners, agrochemical formulations, coatings, fuel treatments, oil cleaners, oil recovery, oil dispersants, disinfectants, water treatments, bleaches, detergents, stain removers, soaps, oily soil cleaners, grease cutters, soft surface cleaners or hard surface cleaners comprising the composition of any one of aspects 14-26 and/or the trialkylamines of any one of aspects 1-13.

In aspect 28, this invention provides dish detergents, kitchen surface cleaners, bathroom surface cleaners, upholstery cleaners, laundry stain removers, carpet cleaners, carpet spot removers, or laundry detergents comprising the composition of any one of aspects 14-26 and/or the trialkylamines of any one of aspects 1-13.

In aspect 29, this invention provides the grease cutters of aspect 27 which are effective at oily soils such as sebum, palm or coconut oil, or animal fat.

In aspect 30, this invention provides a laundry detergent comprising at least one of the trialkylamine oxides of any one of aspects 1-13 having at least a 1% or 2% or 3% or 4% or 5% or 6% or 7% or 8% or 9% or 10% or 11% or 12% or 13% or 15% increase in total stain removal index according to ASTM Method D4265, for example, a 2% to 11% increase or a 3 to 11% increase in total stain removal index according to ASTM Method D4265.

In aspect 31, this invention provides the laundry detergent of aspect 30 comprising a commercial laundry liquid comprising ethoxylated lauryl alcohol, sodium laureth sulfate, sodium carbonate, tetrasodium iminosuccinate, acrylic polymer and stilbene disulfonic acid triazine brightener, but containing no enzymes, dyes or fragrance, for example, the detergent can be ALL FREE CLEAR made by Henkel Corporation, USA.

In aspect 32, this invention provides a process for making any of the trialkylamine oxides of any one of aspects 1-13.

In aspect 33, this invention provides the process of aspect 32 which includes oxidation of trialkylamines useful in this invention, for example, branched C10-C12 N, N-dimethylalkylamines, in a solvent system comprising a polar protic solvent.

In aspect 34, this invention provides the process of aspect 33 wherein the polar protic solvent is an alcohol.

In aspect 35, this invention provides the process of aspect 34 wherein the solvent system comprises alcohol and water.

In aspect 36, this invention provides the process of any one of aspects 34-35 wherein the alcohol is ethanol or isopropanol.

In aspect 37, this invention provides the process of any one of aspects 35-36 wherein the ratio by volume of water to alcohol is from 1:1 to 10:1, or from 2:1 to 5:1, or 3:1, or 4:1.

In aspect 38, this invention provides the process of any one of aspects 32-37 wherein the branched N, N-dimethylalkylamines useful in the invention, for example, C10-C12 branched N, N-dimethylalkylamines, are oxidized to trialkylamine oxides using hydrogen peroxide.

In aspect 39, this invention provides the process of aspect 38 wherein the amount of hydrogen peroxide and tertiary amine useful in this invention is present in the range of about 10:1 to about 1:1, or about 5:1 to about 1:1, or about 4:1 to about 1:1, or about 3:1 to about 1:1 of moles of hydrogen peroxide per mole of tertiary amine; or wherein the molar ratio of hydrogen peroxide to tertiary amine is from 10:1, or 9:1, or 8:1, or 7:1, or 6:1, or 5:1, or 4:1, or 3:1, or 2:1 or 1:1.

In aspect 40, this invention provides the process of aspect 39 wherein the amount of hydrogen peroxide and tertiary amine useful in this invention is present in the range of about 3:1 to about 1:1 moles of hydrogen peroxide per mole of tertiary amine In aspect 41, this invention provides the process of aspect 40 wherein the amount of hydrogen peroxide and tertiary amine is present in the range of about 1-3:1 moles of hydrogen peroxide per mole of tertiary amine.

In aspect 42, the invention provides a process of any one of aspects 32-41 of making an trialkylamine oxide with at least one trialkylamine having the formula:

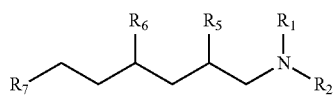

wherein $R_1$ and $R_2$ are each independently selected from straight or branched chain or cyclic hydrocarbon radicals having 1 to 8 carbon atoms;

wherein $R_5$, $R_6$ and $R_7$ are independently at least one of C3H7, C2H5, CH3, or H, or combinations thereof; and wherein $R_5$ and $R_6$ are not H at the same time.

In aspect 43, the invention provides the process of aspect 42 wherein (a) $R_1$ and $R_2$ are each independently substituted with groups selected from: —OR3; carboxyl; —NHCOR4; —CONHR4; cyano; —CO2R3; —OCOR3; hydroxy; aryl; heteroaryl; chlorine; or a combination thereof, (b) R3 is selected from C1-C6 alkyl, substituted C1-C6 alkyl or combinations thereof and (c) R4 is selected from C1-C4 alkyl or substituted C1-C15 alkyl.

In aspect 44, the invention provides the process of aspects 42 or 43 selected from the group consisting of alkyl dimethyl amines or N,N-dimethylalkylamines.

In aspect 45, the invention provides the process of any one of aspects 42-44 wherein $R_1$ can be CH3 or C2H5 and/or $R_2$ can be CH3 or C2H5.

In aspect 46, the invention provides the process of aspect 45 wherein $R_1$ is CH3.

In aspect 47, the invention provides the process of aspects 45 or 46 wherein $R_2$ is CH3.

In aspect 48, the invention provides the process of aspects 45 or 47 wherein $R_1$ can be C2H5.

In aspect 49, the invention provides the process of aspects 45, 46, wherein $R_2$ is C2H5 or the process of aspect 48 wherein $R_1$ and $R_2$ are each independently C2H5.

In aspect 50, the invention provides the process of any one of aspects 42-43 wherein $R_1$ is CH3 or C2H5 and $R_2$ is a carbohydrate or amino acid.

In aspect 51, the invention provides the process of any one of aspects 42-50 wherein $R_5$ and $R_6$ are C3H7, C2H5, CH3, or combinations thereof; and wherein $R_7$ is one of C3H7, C2H5, CH3, H or combinations thereof.

In aspect 52, the invention provides the process of aspect 51 wherein $R_5$ is CH3 or C2H5 and/or $R_6$ is CH3 or C2H5.

In aspect 53, the invention provides the process of aspect 52 wherein $R_5$ is CH3.

In aspect 54, the invention provides the process of aspects 52 or 53 wherein $R_6$ is CH3.

In aspect 55, the invention provides the process of aspects 52 or 54 wherein $R_5$ can be C2H5.

In aspect 56, the invention provides the process of aspects 52, 53, wherein $R_6$ can be C2H5 or the process of aspect 55 wherein $R_1$ and $R_2$ are each independently C2H5.

In aspect 57, the invention provides the process of any one of aspects 42-43 wherein $R_1$ is CH3 or C2H5 and $R_2$ is a carbohydrate or amino acid.

In aspect 58, the invention provides the process of any one of aspects 42-57 wherein the trialkylamine oxide has one to three branch points.

In aspect 59, the invention provides process of any one of aspects 42-58 wherein the trialkylamine oxide has one to three branch points wherein up to 2 branch points occur at the $R_5$ and/or $R_6$ positions.

In aspect 60, the invention provides the process of any one of aspects 42-59 wherein the trialkylamine oxide has two branch points which are at the $R_5$ and $R_6$ positions.

In aspect 61, the invention provides the process of any one of aspects 42-60 wherein the number of carbon atoms for the alkyl substituent at the $R_5$ position of the trialkylamine oxide can be from 1 to 3.

In aspect 62, the invention provides the process of any one of aspects 42-61 wherein the number of carbon atoms for the alkyl substituent at the R6 position of the trialkylamine oxide can be from 1 to 3.

In aspect 63, the invention provides the process of any one of aspects 42-62 wherein the number of carbon atoms for the alkyl substituent at the R5 position of the trialkylamine oxide can be from 1 to 2.

In aspect 64, the invention provides the process of any one of aspects 42-63 wherein the number of carbon atoms for the alkyl substituent at the R6 position of the trialkylamine oxide can be from 1 to 2.

In aspect 65, the invention provides the process of making at least one trialkylamine oxide with at least one trialkylamine selected from 4-ethyl-N,N,2-trimethyloctan-1-amine, 4-ethyl, 2-methyl, N,N-dimethylhexan-1-amine, or 2,4-diethyl, N,N-dimethyloctan-1-amine.

In aspect 66, aldehydes useful in making the trialkylamines useful in the present invention can contain aliphatic hydrocarbon chains, linear or branched, saturated or unsaturated, comprising 2 to 30 carbon atoms.

In aspect 67, aldehydes useful in making the trialkylamines useful in the present invention and/or made using the quaternary ammonium compounds of the invention of any one of aspects 1-10 or 20-22, for example, can be branched C8-C20 aldehydes, for example, 2-ethylhexanal, 2-propylpentanal, 2-propyl-hexanal, 2-propyl-heptanal, 2-propyl-octanal, 2,4-diethyloctanal, 2-ethyl-4-methyl-nonanal, 2-ethyl-4-methyloctanal, or 2-butyl-4-ethyloctanal or combinations thereof.

In aspect 68, examples of enals or aldehydes useful in making any one of the the trialkylamines useful in the invention, for example, can include but are not limited to as follows: examples of C10 to C12 enals include but are not limited to: 4-ethyl-2-methyloct-2-enal (C11 enal), 2,4-diethyl-2-octenal (C12 enal), 2-propyl-heptenal(C10 enal), or 2-ethyl-4-methyl heptenal (C10 enal); Examples of C10 to C12 aldehydes include but are not limited to: aldehyde-4-ethyl-2-methyloctanal (C11 aldehyde), 2,4-diethyl-2-octanal (C12 aldehyde); 2-propyl-heptanal (C10 aldehyde), and 2-ethyl-4-methyl heptanal (C10 aldehyde).

In aspect 69, this invention provides at least one-quaternary ammonium compound made from any one of the trialkylamines useful in making the trialkylamine oxides described in aspects 1-13.

In aspect 70, this invention provides a process wherein at least one quaternary ammonium compound is used as a phase transfer catalyst in making any one of the enals and/or aldehydes useful in making the trialkyl amines which are useful in making the trialkylamine oxides described in aspects 1-13.

In aspect 71, this invention provides aspects 69 or 70 wherein the quaternary ammonium compound comprises the following formula:

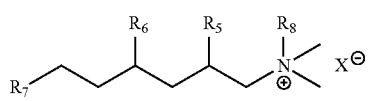

wherein R8 is methyl, ethyl, butyl, or benzyl, and X is a halide or alkosulfate, wherein R5, R6 and R7 are independently at least one of C3H7, C2H5, CH3, or H; and wherein R5 and R6 are not H at the same time.

In aspect 72, this invention provides aspect 71 wherein the quaternary ammonium compound comprises the formula:

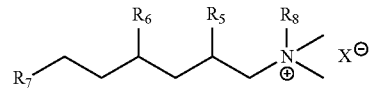

wherein R5 and R6 are C3H7, C2H5, CH3, or mixtures thereof; and
wherein R7 is one of C3H7, C2H5, CH3, H or mixtures thereof.

In aspect 73, this invention provides the quaternary ammonium compounds of any one of aspects 71-72 wherein R6 is CH3 or C2H5.

In aspect 74, this invention provides the quaternary ammonium compounds of any one of aspects 71-73 wherein R5 and R6 independently are C2H5.

In aspect 75, this invention provides the quaternary ammonium compound of any one of aspects 71-73 wherein R5 is CH3 or CH2H5.

In aspect 76, this invention provides the quaternary ammonium compound of any one of aspects 71-73 or 75 wherein R5 is CH3 and R6 is C2H5.

In aspect 77, this invention provides the quaternary ammonium compound of any one of aspects 71-76 wherein R8 is benzyl or butyl.

In aspect 78, this invention provides the quaternary ammonium compound of any one of aspects 71-77 wherein X− is halide.

In aspect 79, this invention provides the quaternary ammonium compound of aspect 78 wherein the halide is selected from chloride, bromide or iodide.

In aspect 80, this invention provides the quaternary ammonium compound of any one of aspects 71-79 selected from N-benzyl-2,4-diethyl-N,N-dimethyloctan-1-aminium chloride or N-butyl-2,4-diethyl-N,N-dimethyloctan-1-aminium bromide.

In aspect 81, this invention provides the process of any one of aspects 71-77 wherein the alkylating agent selected to make the quaternary ammonium compound is selected from at least one of C1-C4 alkyl chloride, C1-C4 alkyl bromide or C1-C4 alkyl iodide, benzyl chloride, benzyl bromide or benzyl iodide, or mixtures thereof.

In aspect 82, wherein the alkylating agent of aspect 81 can be selected from at least one of methyl chloride, ethyl chloride, propyl chloride, butyl chloride, methyl bromide, ethyl bromide, propyl bromide, butyl bromide, benzyl chloride, benzyl bromide or mixtures thereof.

In aspect 83 this invention provides the quaternary ammonium compound of any one of aspects 81-82 wherein the alkylating agent is C1-C4 alkyl bromide.

In aspect 84, this invention provides the quaternary ammonium compound of aspect 83 wherein the alkyl bromide is butyl bromide or any isomers thereof.

DETAILED DESCRIPTION OF THE INVENTION

The present invention may be understood more readily by reference to the following detailed description of certain embodiments of the invention and the working examples. In accordance with the purpose(s) of this invention, certain embodiments of the invention are described in the Summary of the Invention and are further described herein below. Also, other embodiments of the invention are described herein.

Unless otherwise indicated, all numbers expressing quantities of ingredients, properties such as molecular weight, reaction conditions, and so forth used in the specification and claims are to be understood as being modified in all instances by the term "about." Unless indicated to the contrary, the numerical parameters set forth in the following specification and attached claims are approximations that may vary depending upon the desired properties sought to be obtained by the present invention. At the very least, each numerical parameter should be construed in light of the number of reported significant digits and by applying ordinary rounding techniques. Further, the ranges stated in this disclosure and the claims are intended to include the entire range specifications and not just the endpoint(s). For example, a range stated to be 0 to 10 is intended to disclose all whole numbers between 0 and 10 such as, for example 1, 2, 3, 4, etc., all fractional numbers between 0 and 10, for example 1.5, 2.3, 4.57, 6.1113, etc., and the endpoints 0 and 10.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in its respective testing measurements.

As used in the specification and the appended claims, the singular forms "a," "an" and "the" include their plural referents unless the context clearly dictates otherwise. The terms "containing" or "including" are intended to be synonymous with the term "comprising", meaning that at least the named compound, element, particle, or method step, etc., is present in the composition or article or method, but does not exclude the presence of other compounds, catalysts, materials, particles, method steps, etc., even if the other such compounds, material, particles, method steps, etc., have the same function as what is named, unless expressly excluded in the claims.

Also, it is to be understood that the mention of one or more process steps does not preclude the presence of additional process steps before or after the combined recited steps or intervening process steps between those steps expressly identified.

In one embodiment, this invention provides novel compositions which can be used to produce novel surfactants. This invention also provides effective reactants and processes to make the branched surfactants and corresponding surfactant intermediates with fewer reaction byproducts, fewer reaction steps, and/or reduced reaction solvent.

As used herein the term "hydrophobe" means a molecule that can serve as the hydrophobic, or non-polar segment of a surface-active compound or surfactant. The branched $C_{10}$-$C_{12}$ hydrophobes useful in this invention and their surfactant derivatives are often liquids at room temperature, the surfactants are typically low foaming and may be mild to skin. Surfactants made from the branched hydrophobes can have improved solubility in water and can interact differently with other ingredients in a formulation. They can also have altered biological activity that can provide beneficial activity (such as antimicrobial, antifungal, and/or antiviral activity) or safety (such as reduced aquatic toxicity, reduced skin irritation, reduced irritation to eyes and mucous membranes, reduced allergenicity or tendency to cause contact dermatitis). As a result, the surfactants derived from branched trialkylamine hydrophobes can have properties well-suited for use in personal and home care applications, which value these traits in formulating, use and disposal of the surfactants.

In one embodiment, this invention provides novel compositions which can be used to produce novel compositions, e.g., surfactants, with one or more of the following desirable properties: (1) low foaming, such as according to ASTM E2407, (2) mildness to skin, such as predicted by a zein solublization test or patch test, (3) effective oily soil and/or stain removal, especially in cold water, such as according to ASTM 4265, (4) compatibility with other ingredients in a cleaning formula, and (5) a favorable environmental profile, (6) high solubility in water; (7) no gelling, (8) ease of formulation, and (9) compatibilization or stabilization of other ingredients in a formula, (10) retains good hydrophobicity compared to linear hydrophobes, (11) tolerance of extreme pH, (12) antimicrobial activity, (13) biodegradability, such as according to OECD 301B and/or (14) an improved safety profile. This invention also provides effective reactants and processes to make branched surfactants and corresponding surfactant intermediates with fewer reaction byproducts, fewer reaction steps, and/or reduced reaction solvent.

In another embodiment, the compositions of this invention can provide one or more of the following properties: (1) low foaming, (2) effective oily soil and/or stain removal, especially in cold water, (3) high solubility in water; (4) no gelling, (5) ease of formulation, (6) compatibilization or stabilization of other ingredients in a formula, (7) tolerance of extreme pH, (8) biodegradability, and/or (9) an improved safety profile.

Low foaming characteristics in combination with improved cleaning performance such as more effective soil and/or stain removal is important for laundry and dishwashing formulations where low foaming results in greater efficiency and durability of dishwashers, washing machines, upholstery and rug cleaners or other appliances utilizing them. Also, higher solubility in water and/or no gelling enable the compositions of the invention to be placed in a more concentrated liquid form prior to transfer, transport for both reactions and formulations. Branched surfactants can also reduce the viscosity of the formulation(s) that they are in which can provide benefits like easier dispensing and reduction in the requirement for added water in the formulation.

In one embodiment, the invention provides trialkylamine hydrophobes. In another embodiment, the invention provides branched enals and aldehydes useful in making the trialkylamines useful in the invention. The trialkylamines useful in the invention are useful in making the (1) trialkylamine oxides of the invention and (2) the quaternary ammonium salts or "quats" useful as phase transfer catalysts in making the trialkyl amines useful in the invention.

The invention also provides surfactants made from the branched trialkylamine intermediates of the invention, including amphoteric, cationic and nonionic surfactants, for example, trialkylamine oxides.

In the present invention, enals and aldehydes with more than one branch point useful in the invention can be produced by a combination of hydroformylation and aldol condensation. In one embodiment, the enals and aldehydes have two branch points. For example, 2-ethylhexanal can be reacted with either propionaldehyde or n-butyraldehyde in a crossed aldol reaction to produce a C11 or C12 enal. Alternately, the self-condensation product of propionaldehyde can be reacted with n-butyraldehyde to produce a C10 enal with two branch points. Examples of the reactions and products are depicted below. The C10 to C12 enals can be further hydrogenated to the corresponding aldehyde or alcohol.

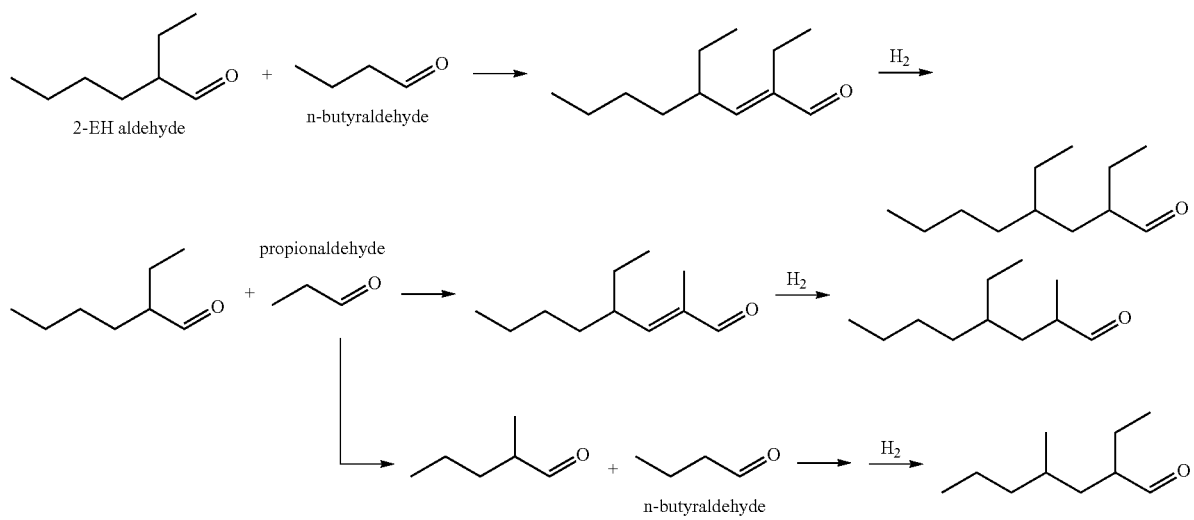

Aldol condensation reactions, or aldolization reactions, are known in the art. Two types of aldol condensation reactions frequently encountered are the self-aldol condensation (Aldol I) and cross-aldol condensation (Aldol II) reactions. In an Aldol I reaction, two molecules of the same aldehyde starting material react to form a reaction product. Alternatively, in an Aldol II reaction, two different aldehyde starting materials react to form a reaction product.

The reaction between two of the same aldehyde molecules is a classic case with an equilibrium far to the right. In practice, the condensation of two molecules of the same aldehyde (Aldol I) to form an aldol can be followed immediately by dehydration to form an unsaturated aldehyde with twice the original number of carbon atoms.

In an Aldol II reaction, however, the condensation of two molecules of different aldehydes forms an aldol and, upon dehydration, further forms an unsaturated aldehyde having the sum of the carbon atoms of the two different aldehydes. Both Aldol I and Aldol II reactions are well known in the art, as are the conditions required to affect their condensation.

The C10 to C12 aldehydes useful in the invention are formed by reacting at least one aldehyde starting material in the presence of a basic catalyst to form aldol condensation products.

In one embodiment, the aldehyde starting materials can include but are not limited to C2 to C8 aldehydes selected from the group consisting of acetaldehyde, propionaldehyde, n-butyraldehyde, isobutyraldehyde, valeraldehyde, 2-ethylbutyraldehyde, 2-methylpentanal, 2-ethylhexanal or mixtures thereof. although other aldehydes can also be suitable.

The aldol condensation can be enacted in a single step, as in the crossed aldol reaction of n-butyraldehyde and 2-ethylhexanal, or in more than one step, as in the aldol condensation or propionaldehyde to form 2-methyl-2-pentenal followed by hydrogenation to 2-methylpentanal, then a crossed aldol reaction between 2-methylpentanal and n-butyraldehyde to form 2,4-dimethyl-2-heptenal. U.S. Pat. No. 6,090, 986 to Godwin et al. discloses an example of Aldol II in the formation of 2,4-dimethyl-2-heptenal from condensing 2-methyl-pentanal and propanal.

The cross aldol or homoaldol reactions run in utilization of this invention can be catalyzed by the addition of a base. A base can be defined in many ways such as any substance that releases hydroxide ions (OH⁻) upon dissolution in water or a substance that accepts a proton (Bronsted-Lowry theory). A base can also be any substance that donates an electron pair (Lewis Theory) [Whitten and Gailey, 1981].

In the invention, the aldol reactions can be catalyzed by any substance or substances meeting any of the definitions described herein or in the art of a base. In the invention, the aldol reactions can be catalyzed by any substance or substances meeting any of the definitions described herein or in the art of a base. In one embodiment, the base can be any hydroxide, bicarbonate, or carbonate salt of the Group I or Group II metals; NaOH; KOH; $NaHCO_3$; $Na_2CO_3$; LiO; CsOH; sodium methoxide; sodium ethoxide; sodium propoxide; potassium methoxide; potassium butoxide; cesium methoxide, or the like, or mixtures thereof. In one embodiment, the catalysts can include NaOH, NaHCO3, KOH, or K2CO3.

In one embodiment, the base can be any hydroxide, bicarbonate, or carbonate salt of the Group I or Group II metals. In another embodiment, the base can be one or more selected from NaOH, KOH, $NaHCO_3$, $Na_2CO_3$, LiOH, CsOH, and the like. In another embodiment, the basic catalyst (base) can also be chosen from sodium methoxide, sodium ethoxide, sodium propoxide, potassium methoxide, potassium butoxide, cesium methoxide, or the like. In another embodiment, the base is NaOH. When the base is NaOH, using a ratio of 1.15 to 1.25 of NaOH:nHbu can provide an enal yield of at least 40%.

The catalyst can also be other organic or inorganic bases and can, for example be carbonates, bicarbonates, phosphates, pyrophosphates, and hydrogenphosphates of alkali metals, and/or it may include quaternary ammonium compounds, tertiary amines, ion exchange resins, guanidine derivatives, amidine compounds, and combinations thereof. In one embodiment, tertiary amines can be the catalyst. In another embodiment, the catalyst can be NaOH. The concentration of the basic catalyst can be varied, but molar or similar concentrations of alkali metal hydroxides can be used, and concentrations selected will generally be in the range of about 1 to 50% or 1 to 30% or 1 to 25% 5 to 50% or 5 to 30% or 5 to 25% by weight based on the total weight of the composition. The amount of aqueous alkali to aldehyde reactant can also vary, for example, from about 15% by volume aqueous alkali up to about 75% by volume aqueous alkali. In one embodiment, the amount of aqueous alkali to aldehyde reactant can also vary, for example from about 20% by volume aqueous alkali up to about 45% by volume aqueous alkali. In yet another embodiment, the amount of aqueous alkali to aldehyde reactant can also vary, for example, from about 25% by volume aqueous alkali up to about 35% by volume aqueous alkali.

The base catalyst, especially the most commonly used bases, NaOH, KOH, NaHCO$_3$, and the like, are introduced as aqueous solutions to the reaction mixture. As the chain length of the raw material aldehyde or ketone increases, the solubility of the base in the organic reaction medium can decrease. For instance, two molecules of 4 carbon n-butyraldehyde readily react in aqueous caustic, but one molecule of n-butyraldehyde and one molecule of 8 carbon 2-ethylhexanal may not react in the same basic solution. In order to increase the solubility of the longer chain molecule, a phase transfer catalyst (PTC) is used.

Phase transfer catalysts shuttle ions across organic and aqueous phase boundaries. A phase transfer catalyst (PTC) is effective in improving conversion in this procedure. In many cases, the phase transfer catalyst is a quaternary ammonium salt. The PTC can be any quaternary ammonium salt capable of transmitting organic and aqueous components across a phase boundary. The quaternary ammonium salt could be a pure component or a mixture of salts. Typical quaternary ammonium salts are comprised of tetra alkyl or tetra aromatic ammonium cations and a counter anion. Counter anions include halogens or polyatomic ions such as BF$_4$, PF$_6$, SO$_2$, SO$_4$, or the like. Common PTCs include tetrabutyl ammonium chloride, tetrabutyl ammonium bromide, tetrabutyl ammonium iodide, tetramethyl ammonium chloride, and benzalkyl ammonium chloride. The use of co-solvents, such as methanol or diols, may also be used. The concentration of PTC can vary.

To avoid the formation of byproducts, such as Hoffman Elimination byproducts, from PTC such as tetrabutyl ammonium salts or mixtures of alkyl benzyl ammonium salts, this invention provides a phase transfer catalyst utilizing an amine derived from the aldehydes useful in the invention, for example, a C10, C11 or C12 aldehyde. For example, 2,4-diethyl-octenal, produced by the cross aldol reaction of n-butyraldehyde and 2-ethylhexanal, can be combined with N,N-diethylamine over a copper catalyst to produce 2,4-diethyl-N,N-dimethyloctan-1-amine. The product amine can then be reacted with benzyl chloride to form the PTC in excellent yield. Similarly, the product amine can be reacted with an alkyl chloride (ethyl chloride, propyl chloride, butyl chloride) to generate a PTC. In one embodiment, one quarternary ammomium salt of the invention is N-benzyl-2,4-diethyl-N,N-dimethyl-octyl ammonium chloride.

The resultant phase transfer catalyst is similar in structure to any of the components of the mixture alkyldimethylbenzylammonium chloride, but is comprised of a single molecule. Its resultant use in cross aldol reactions can deliver similar or superior yields to BAC and to other PTCs described in the art, with the added benefit of producing a single high boiler component as identified by gas chromatography. The aldol products are easily separated from this single high boiler by distillation.

In one embodiment, a PTC useful in the invention can be used in the cross aldol reaction of n-butyraldehyde and 2-ethylhexanal to produce 2,4-diethyloctenal in reasonable yield. The PTC can also be used in any aldol condensation involving any two aldehydes compound containing a carbon chain from 1-20 carbons. Such aldehydes include formaldehyde, acetaldehyde, propionaldehyde, butyraldehyde, 2-methyl-propionaldehyde, valeraldehyde (1-pentanal), isovaleraldehyde (2-methyl-butyraldehyde), hexanal, 2-ethylhexanal, 1-octanal, 1-nonanal, and the like. The reaction utilizing this invention can contain two or more different aldehydes (cross aldol) of two or more molecules of the same aldehyde (homoaldol).

The aldol condensation reaction can be performed in an aqueous solution, in an organic solvent, or in a mixture of water and an organic solvent. Such organic solvents include methanol, ethanol, propanol, butanol, acetone, acetonitrile, pentane, hexane, heptane, cyclohexane. The solvent can also be any of the starting aldehydes or product aldehydes useful in the invention.

The reactions for forming aldol condensation products can be generally carried out at a pressure of from about 1 atm (atmospheric pressure) to about 1000 atm (elevated pressure) or from about 1 atm to about 500 atm, or from about 1 to about 300 atm, or from about 1 to about 100 atm, or from about 1 to about 50 atm, or from about 1 to about 20 atm. The reaction can be carried out over a wide range of temperatures and is not particularly limited. The reaction temperature can be within the range of from about −20° C. to 300° C., for example, within the range of from 20° C. to 100° C.

The reaction can be run at ambient temperature and pressure. Increased conversion can be accomplished by running at higher temperature or pressure. In one embodiment, the reaction can be run between 20° C. and 70° C. In another embodiment, the reaction can be run between 50° C. and 70° C.

The reaction temperature can be increased by running the reaction at higher pressures. In one embodiment, the reaction can be run anywhere from 100 kPa to 2000 kPa. In another embodiment, the reaction can be run from 100 to 1000 kPa. In yet another embodiment, the reaction can be run at ambient (atmospheric) pressure.

The aldol reaction can be run for a sufficient time to obtain the desired degree of conversion. The aldol condensation reactions can run for about 1 to 10 hours or 1 to 3 hours. They can be run as batch or continuous reactions. When run as continuous reactions, the residence time can be substantially shorter than 3 hours, for example, less than 2 hours, less than 1 hour, less than 30 minutes, less than 10 minutes, or less than 5 minutes. In one embodiment, batch reactions can be run in the range of about 30 minutes to about 3 hours or about 1 to about 3 hours.

The reaction can be stopped by permitting the reaction mixture to cool and separating the organic reaction phase from the aqueous alkali phase. The saturated or unsaturated aldehyde can be purified prior to further conversion, or may be used directly. Purification of the saturated or unsaturated aldehyde can be effected by decanting, extraction, distillation, filtration or chromatographic separation.

Following the aldol condensation step, the unsaturated product can be hydrogenated to produce the saturated aldehyde, which can be further hydrogenated to form the alcohol or, alternatively, can be oxidized to form the carboxylic acid. The unsaturated aldehyde or enal can be used directly as a substrate for reductive amination.

Examples of C10 to C12 enals useful in this invention include but are not limited to: 4-ethyl-2-methyloct-2-enal (C11 enal), 2,4-diethyl-2-octenal (C12 enal), 2-propyl-heptenal(C10 enal), or 2-ethyl-4-methyl heptenal (C10 enal); Examples of C10 to C12 aldehydes include but are not limited to: aldehyde-4-ethyl-2-methyloctanal (C11 aldehyde), 2,4-diethyl-2-octanal (C12 aldehyde); 2-propyl-heptanal (C10 aldehyde), and 2-ethyl-4-methyl heptanal (C10 aldehyde).

Examples of products that can be made with the C10 to C12 enals and/or aldehydes useful in the invention are: (A.) Trialkylamines: The C10 to C12 enal or aldehydes described herein may be reacted with dialkyl amines such as dimethylamine to obtain N,N-dimethylalkylamines as surfactant intermediates. Similarly, the C10 to C12 enal or aldehydes can be reacted with diethanolamine, dipropylamine, diisopropylamine to obtain the corresponding trialkylamine; the trialkylamines decribed herein can be used to make other products such as (B.) Quaternary Ammonium Compounds useful in the invention; and/or (C.) Trialkylamine Oxides of the invention, as follows:

A. Trialkylamines Useful in the Invention

In one embodiment, the C10 to C12 enal or aldehydes useful in the invention can be reacted with dialkyl amines such as dimethylamine to obtain N,N-dimethylalkylamines which can be useful, for example, as surfactant intermediates. Similarly, the C10 to C12 enal or aldehydes can be reacted with diethylamine, dipropylamine, or diisopropylamine to obtain the corresponding trialkylamines.

Among the more versatile surfactant intermediates are the trialkylamines, also called tertiary amines. In the present invention, C10 to C12 enals or aldehydes are reacted with a secondary amine under reductive conditions to produce trialkylamines useful in the invention.

Reductive amination processes are well known in the art for the synthesis of primary, secondary and tertiary amine. The term "amination" relates to the reaction part in which an amine functionality is incorporated into the substrate. The term "reductive" relates to the observation, when comparing the feed substrate and the product of a reductive amination reaction, that a reduction has necessarily also taken place. In chemistry, a reduction reaction refers in general to the gain of electrons of an atom or a molecule. In organic chemistry, reductions are usually related with the disappearance of unsaturated functionality, such as double bonds, from the substrate molecules. The net result of a reductive amination of a ketone or aldehyde is the conversion of a C=O double bond into a C—N single bond.

The reductive amination of ketones or aldehydes towards trialkylamines can be done in either one or two process steps in which the first step comprises the reaction of the ketone or aldehyde with an amination reagent such as dimethylamine to form an intermediary imine or enamine followed by the second process step in which the intermediary imine or enamine is hydrogenated towards the desired amine. The reductive amination reaction of ketones or aldehydes can be done in a gas- or liquid-phase process in the presence of a reducing agent, an amine and if deemed necessary, a suitable catalyst. The reductive amination reaction can be performed in a reaction medium comprising a solvent. In the context of the present invention, a solvent is a compound which does not take part in the chemical reaction and which is capable of reducing the concentration in the reaction medium of any of the other compounds, such as reagents, catalysts and reaction products.

As for other hydrogenation reactions, stoichiometric reagents are sometimes used as reducing agents, for example, formic acid or hydrides such as borohydrides or aluminium hydrides. In one embodiment, hydrogen can be used as the reducing agents. Suitable catalysts can be either heterogeneous or homogeneous hydrogenation catalysts. In one embodiment, hydrogenation catalysts can comprise at least one active metal, either in elementary form or in the form of a compound, for example, oxides. Examples of catalysts containing metals in their elementary form are Raney-nickel and Raney-cobalt. In one embodiment, the catalyst comprises a mixture of active metals. The metals can be present in ionic form or as covalently bound. When oxides of the active metals are used, the process can comprise a reduction of the oxide to the elementary metal, typically at higher temperatures, for example, 300° C. to 700° C. (the temperature used in typically determined by the metal and is referred to as "calcining"), and, for example, can be in the presence of hydrogen. Useful hydrogenation catalysts can be selected from one or more of the metals of groups IVb, Vb, Vlb, Vllb, Vlllb, lb or Ilb. In one embodiment, catalysts containing nickel, palladium, platinum, cobalt, rhodium, iridium, copper, manganese, tin or ruthenium can be used.

This reaction can be performed either batch wise or continuous. If a continuous installation is used, this can be either a continuous stirred tank reactor (CSTR) or plug flow reactor. The temperature can range from 80 to 300° C. and the pressure from 1 bara to 100 bara. As used herein, "bara" means (Absolute Pressure) Pressure reading relative to absolute vacuum.

The reaction can be performed in an excess of the ketone or aldehyde, in an excess of the amination agent such as dimethylamine or in stoichiometric amounts of the two reagents. The amination reagent may be added in a 10:1 to 1:1 molar ratio, or based on the enal or aldehyde reactant, preferably 5:1 to 1:1; or 4:1 to 1:1; or 4:1 to 2:1; or 3:1 or 4:1.

In one embodiment, the C10 to C12 enal or aldehydes useful in the invention may be reacted with dimethylamine under reductive conditions to obtain alkyl dimethyl amines, or N,N-dimethylalkylamines useful in the invention. In one embodiment, the trialkylamines useful in making the trialkylamine oxides of the invention can be selected from one 4-ethyl-N,N,2-trimethyloctan-1-amine, 4-ethyl, 2-methyl, N,N-dimethylhexan-1-amine, or 2,4-diethyl, N,N-dimethyloctan-1-amine.

In one embodiment, the invention includes a trialkylamine having the formula:

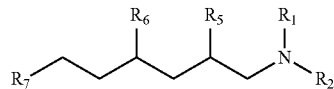

wherein R1 and R2 are each independently selected from straight or branched chain or cyclic hydrocarbon radicals having 1 to 8 carbon atoms;

wherein R5, R6 and R7 are independently at least one of C3H7, C2H5, CH3, or H, or combinations thereof; and wherein R5 and R6 are not H at the same time.

In one embodiment, for the trialkylamine, (a) R1 and R2 can be each independently substituted with groups selected from: —OR3; carboxyl; —NHCOR4; —CONHR4; cyano; —CO$_2$R3; —OCOR3; hydroxy; aryl; heteroaryl; chlorine; or a combination thereof, (b) R3 can be selected from C$_1$-C$_6$ alkyl, substituted C$_1$-C$_6$ alkyl or combinations thereof and (c) R4 can be selected from C$_1$-C$_4$ alkyl or substituted C$_1$-C$_{15}$ alkyl.

In one embodiment, for the trialkylamine, R1 and R2 independently can be CH3; in one embodiment, R1 can be CH3 or C2H5; in one embodiment, R2 can be CH3 or C2H5; in one embodiment, R1 and R2 independently can be C2H5.

In one embodiment, for the trialkylamine, R1 can be CH3 when R2 is C2H5, or R1 can be CH2H5 when R2 is CH3.

In one embodiment, for the trialkylamine, R1 can be CH3 or C2H5 and R2 can be a carbohydrate or amino acid.

In one embodiment, for the trialkylamine, R5 and R6 can be C3H7, C2H5, CH3, or combinations thereof; and wherein R7 can be one of C3H7, C2H5, CH3, H or combinations thereof. In one embodiment, for the trialkylamine, R5 can be CH3 or C2H5; in one embodiment, R6 can be CH3 or C2H5; in one embodiment, R5 and R6 independently can be CH3; in one embodiment, R5 and R6 independently can be C2H5. In one embodiment, for the trialkylamine, R5 can be CH3 when R6 is C2H5, or R5 can be CH2H5 when R6 is CH3.

In one embodiment, the trialkylamine can have one to three, or one to two, or only two branch points. In one embodiment, the trialkylamine oxide can have three or three or more branch points where two branch points are at the R5 and R6 positions. In one embodiment, the trialkylamine oxide can have one to two branch points at the R5 and/or R6 positions. In one embodiment, the trialkylamine oxide can have two branch points which are at the R5 and R6 positions.

In one embodiment, for the trialkylamine oxide, the number of carbon atoms for the alkyl substituent at the R5 position can be from one to three or one to two.

In one embodiment, the trialkylamine oxides of the present invention can be made from any of the trialkylamines of the present invention.

In one embodiment, for the trialkylamine oxide, the number of carbon atoms for the alkyl substituent at the R6 position can be from one to three or one to two.

In one embodiment, the invention provides a composition comprising at least one trialkylamine oxide or mixture of amine oxides of the invention which are not derived from trialkylamines or mixtures of trialkyl amines containing any isomeric compound or mixtures, wherein said mixtures contain a number of isomeric compounds, and wherein said isomeric compound(s) can be selected from those of structures:

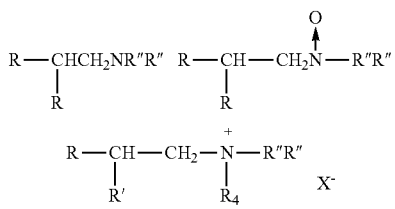

having from 10 to 18 carbon atoms in the R(R')CHCH2- moiety in which R has 5 to 9 carbon atoms, and R' has from 3 to 7 carbon atoms, with most of the compounds having additional methyl or ethyl branches, and in which R''' and R'''' are alkyl or hydroxyalkyl groups or hydrogen and X– is an anion.

In one embodiment, the invention provides a composition comprising at least one trialkylamine oxide or mixture of amine oxides of the invention which are not derived from trialkylamines or mixtures of trialkyl amines containing any isomeric compound or mixtures of isomers as described in the previous paragraph, wherein said mixtures contain a number of isomeric compounds, wherein said isomeric compound(s) can be selected from tertiary amines with a higher branched-chain alkyl substituent characterized as having 10 to 18 carbon atoms and an alkyl branch at the 2-position containing 3 to 7 carbon atoms, and additional branching in most of the isomers, with most of the additional branches being methyl groups.

In one embodiment, the invention provides a composition comprising at least one trialkylamine oxide or mixture of amine oxides of the invention which are not derived from trialkylamines or mixtures of trialkyl amines containing any isomeric compound or mixtures of isomers as described in the previous paragraph, wherein said mixtures contain a number of isomeric compounds, and wherein said isomeric compounds can be selected from tertiary amines with a higher branched-chain alkyl substituent characterized as having 12 carbon atoms and an alkyl branch at the 2-position containing 5 carbon atoms or greater, whether or not with additional branching in most of the isomers, whether or not with most of the additional branches are methyl groups and/or ethyl groups.

In one embodiment, the invention provides a composition comprising at least one trialkylamine oxide of the invention which are not derived from any trialkylamine or mixtures of trialkylamines other than those described herein as being within the scope of this invention.

The trialkylamine oxides of the invention can be surfactants useful for personal care, home care and industrial applications, as well as any other end-use that would be apparent to one of ordinary skill in the art.

B. Quaternary Ammonium Compounds (Quats)

In one embodiment, the enals and/or aldehydes used to make the trialkylamines useful in the invention can be made using a phase transfer catalyst which can be at least one quaternary ammonium compound produced from any one of the trialkylamines or trialkylamine combinations of the invention. The trialkylamines useful in this invention are useful in a process for producing the trialkylamine oxides of the invention.

In one embodiment, this invention provides a process of making the enals and/or aldehydes useful in making the trialkylamines useful in the invention which comprises using as a phase transfer catalyst at least one quaternary ammonium compound comprising the following formula:

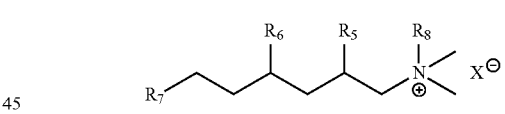

wherein R8 is methyl, ethyl, butyl, or benzyl, and X is a halide or alkosulfate,
wherein R5, R6 and R7 are independently at least one of C3H7, C2H5, CH3, or H; and
wherein R5 and R6 are not H at the same time.

In one embodiment, this invention provides a process of making the enals and/or aldehydes useful in making the trialkylamines useful in the invention which comprises using as a phase transfer catalyst at least one quaternary ammonium compound comprising the following formula:

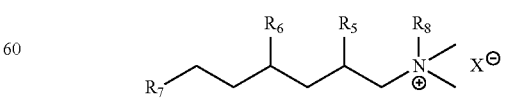

wherein R5 and R6 are C3H7, C2H5, CH3, or mixtures thereof; and
wherein R7 is one of C3H7, C2H5, CH3, H or mixtures thereof.

In one embodiment, for the quaternary ammonium compounds, R5 can be CH3 or C2H5; in one embodiment, R6 can be CH3 or C2H5; in one embodiment, R5 and R6 independently can be CH3; in one embodiment, R5 and R6 independently can be C2H5. In one embodiment, for the quaternary ammonium compound, R5 can be CH3 when R6 is C2H5, or R5 can be CH2H5 when R6 is CH3; R8 can be benzyl or butyl; X– can be halide, for example, chloride, bromide or iodide; in one embodiment, the quaternary ammonium compound can be selected from N-benzyl-2,4-diethyl-N,N-dimethyloctan-1-aminium chloride or N-butyl-2,4-diethyl-N,N-dimethyloctan-1-aminium bromide.

In one embodiment, the invention provides at least one process for using at least one quaternary ammonium compound useful in the invention as a phase transfer catalyst. In one embodiment, the invention provides at least one process wherein the quaternary ammonium compound is used as phase transfer catalyst in a process for making a enal or aldehyde, whether branched or not, for example, any enal or aldehyde useful in making any product of this invention, for example, products including but not limited to trialkylamines (including branched trialkylamines) useful in the invention and/or the trialkylamine oxides of the invention.

Any trialkylamines useful in the invention or combinations thereof can be reacted with alkylating agents such as halides (e.g. methyl chloride) or alkyl sulfates (e.g. dimethyl sulfate) to form the cationic quaternary ammonium salts ("quats") of the invention. The branched C10-12 N,N-dimethylalkylamines useful in the invention can be reacted to form branched C10-C12 quaternary ammonium compounds useful in the invention. For example, branched BAC-b12 (N-benzyl-2,4-diethyl-N,N-dimethyloctan-1-aminium chloride) and N-butyl-2,4-diethyl-N,N-dimethyloctan-1-aminium bromide (branched C12-butyl quat.) are examples of branched C10-C12 quaternary ammonium compounds useful in the invention.

In one embodiment, this invention provides at least one quaternary ammonium compound useful in the invention wherein the alkylating agent selected to make the quaternary ammonium compound can be selected from at least one of C1-C4 alkyl chloride, C1-C4 alkyl bromide or C1-C4 alkyl iodide, benzyl chloride, benzyl bromide or benzyl iodide, or mixtures thereof.

In one embodiment, this invention provides at least one quaternary ammonium compound useful in the invention wherein the alkylating agent can be selected from at least one of methyl chloride, ethyl chloride, propyl chloride, butyl chloride, methyl bromide, ethyl bromide, propyl bromide, butyl bromide, benzyl chloride, benzyl bromide or mixtures thereof. In one embodiment, the alkylating agent can be C1-C4 alkyl bromide.

In one embodiment, the alkylating agent can be the quaternary ammonium compound useful the invention wherein the alkyl bromide is butyl bromide or any isomers thereof.

In one embodiment, the trialkylamine oxides of the invention can be combined with any of the quaternary ammonium compounds of the invention.

C. Trialkylamine Oxides

In one embodiment, this invention provides at least one trialkylamine oxide made from any one of the trialkylamines or trialkylamine combinations or compositions comprising at last one trialkylamine of the invention. In another embodiment, this invention provides a process for making any of the trialkylamine oxides or trialkylamine oxide compositions of the invention.

The trialkylamines can be oxidized at the nitrogen to form tertiary amine-N-oxides. Aliphatic amine oxides (AO) of the invention can be produced by the reaction of the trialkylamines of the invention and hydrogen peroxide. Branched C10-12 N,N-dimethylalkylamines useful in the invention can be oxidized to branched trialkylamine oxides of the invention using hydrogen peroxide. In one embodiment, the amount of hydrogen peroxide to tertiary amine can be present in the range of about 10:1 to about 1:1, or about 5:1 to about 1:1, or about 4:1 to about 1:1, or about 3:1 to about 1:1 moles of hydrogen peroxide per mole of tertiary amine; or where the molar ratio of hydrogen peroxide to tertiary amine can be from 10:1, or 9:1, or 8:1, or 7:1, or 6:1, or 5:1, or 4:1, or 1-3:1, or 3:1, or 2:1, or 1:1, or 1-3:1 moles of hydrogen peroxide per mole of tertiary amine.

An example of a process for the production of amine oxides from N,N-dimethylalkylamines can be found in U.S. Pat. No. 6,037,497. Examples of branched trialkylamine oxides within the scope of the invention are: 4-ethyl-N,N-2-trimethyloctan-1-amine oxide (Branched C11-amine oxide); and 2,4-diethyl-N,N-dimethyloctan-1-amine oxide (Branched C12-amine oxide). Amine oxide synthesis from linear alkyl dimethylamines like dimethyl laurylamine (DIMLA) can be performed in water. The low water-solubility and branching pattern of the branched C10-12 N,N-dimethylalkylamines can reduce the effectiveness of a purely aqueous oxidation reaction. Using water as a sole reaction solvent can result in only trace amounts of product. To increase the reaction efficiency, a polar protic solvent, with or without water, may be used for the oxidation reaction. In one embodiment, an alcohol solvent or mixed solvent system of alcohol and water can be used. In one embodiment, the solvent can be an alcohol/water mixture, and the alcohol is ethanol. The ratio of water to alcohol (for example, ethanol or isopropanol), can be 1:1 to 10:1, or 2:1 to 5:1, 3:1, or 4:1. After the reaction, alcohol can be removed from the reaction mixture at low temperature. The removal of the alcohol, for example, ethanol, can be achieved under vacuum.

The trialkylamine oxides of the invention can be commercially important because of their surfactant properties, and can be used, for example, in liquid dish detergents, in liquid laundry detergents and in agrochemical formulations. They can be nonionic surfactants or cationic surfactants depending on pH. They can be used as surfactants in home care, coatings, fuels, and bleaches. The trialkylamine oxides of the invention can be used in both dish and laundry liquids and in some hard surface cleaners as surfactants and foam boosters. Trialkylamine oxides of the invention can be compatible with formulas across a broad pH range, including highly alkaline formulas, and formulas containing bleach and oxidizing agents like hydrogen peroxide. They can be excellent grease cutters, able to remove a variety of oily soils from surfaces and fabrics. Oily soils that are solid at room temperature or in cold water cleaning, like body soil (sebum), palm or coconut oil, animal fat and wax are especially difficult to remove.

Energy-saving high efficiency (HE) washing machines use cold water and low water volumes for washing laundry. The conventional hot water wash is not energy efficient and, in general, can be detrimental to some sensitive fabrics; therefore milder conditions can be desired in order to remove stains. Effective stain removal from fabric is temperature dependent and therefore there is an increasing demand for laundry detergents that can effectively remove stains at lower temperatures. Long chain amine oxides can be derived from naturally occurring linear C8-C14 alcohols which in turn are primarily obtained from palm and coconut trees. Due to the decline in cultivation and harvesting of these natural resources, the price of these alcohols is often unpredictable. Therefore, there is an increasing demand to use alternate chemical intermediates from feedstock materials for the synthesis of amine oxides that are feasible for cold water wash in high efficiency washing machines. In addition to excellent oily soil removal, the branched trialkylamine oxides of the invention also tend to generate less foam in a formula than their linear counterparts. In high-efficiency (HE) washing machines, excess foam can prolong the rinse cycle, increasing the water used for a load of laundry, defeating the resource efficiency of the appliance.

In one embodiment, this invention provides at least one trialkylamine oxide having the formula:

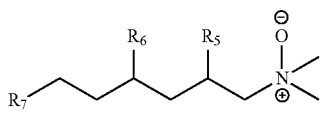

wherein R5, R6 and R7 are independently at least one of C3H7, C2H5, CH3, or H, or mixtures thereof; and wherein R5 and R6 are not H at the same time.

In one embodiment, this invention provides at least one trialkylamine oxide having the formula:

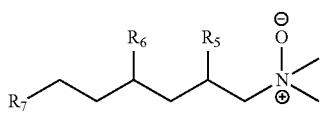

wherein R5 and R6 can be C3H7, C2H5, CH3, or combinations thereof; and
wherein R7 can be one of C3H7, C2H5, CH3, H or combinations thereof.

In one embodiment, for the trialkylamine oxide, R5 can be CH3 or C2H5; in one embodiment, R6 can be CH3 or C2H5; in one embodiment, R5 and R6 independently can be CH3; for the trialkylamine oxide, R5 and R6 independently can be C2H5. In one embodiment, for the trialkylamine oxide, R5 can be CH3 when R6 is C2H5, or R5 can be CH2H5 when R6 is CH3.

In one embodiment, the trialkylamine oxide can have one to three, or one to two, or only two branch points. In one embodiment, the trialkylamine can have one to two branch points at either or both of the R5 and/or R6 positions, respectively. In one embodiment, the trialkylamine can have two branch points which are at the R5 and R6 positions. In one embodiment, the trialkylamine can have three or more than three branch points wherein two branch points are at the R5 and/or R6 positions In one embodiment, for the trialkylamine oxide, the number of carbon atoms for the alkyl substituent at the R5 position can be from one to three or from one to two.

In one embodiment, for the trialkylamine oxide, the number of carbon atoms for the alkyl substituent at the R6 position can be from one to three or from one to two.

In one embodiment, this invention provides at least one trialkylamine oxide which is 2,4-diethyl-N,N-dimethyloctan-1-amine oxide or 4-ethyl-N,N-2-trimethyloctan-1-amine oxide.

In one embodiment, this invention provides any one of the trialkylamine oxides of the invention wherein foaming does not persist for more than 5 minutes when tested according to modified ASTM Method E2407, wherein the method modification is to substitute at least one of said amine oxides for sodium lauryl ether sulfate and to use no defoamer.

In one embodiment, this invention provides any one of the trialkylamine oxides of the invention (for example, 2,4-diethyl-N,N-dimethyloctan-1-amine oxide) having a Zein score of less than 1.0 when normalized to linear alcohol ethoxylate (LAE 10) using the Zein Solubilization Test. In one embodiment, the invention provides any one of the trialkylamine oxides of the invention (for example, 2,4-diethyl-N,N-dimethyloctan-1-amine oxide) having a Zein score of less than 0.50, or less than 0.40, or less than 0.30, or less than 0.20, or less than 0.10, or less than 0.05, or less than 0.02 when normalized to linear alcohol ethoxylate (LAE 10) using the Zein Solubilization Test.

In one embodiment, the invention provides any one of the trialkylamine oxide compositions of the invention comprising 0.05 weight % of trialkylamine oxide in (1500 ml) deionized water which has a Draves wet-out time (WOT) in seconds of greater than 300 seconds, or greater than 200 seconds, or greater than 100 seconds, or greater than 33 seconds, according to Draves Wetting Test or ASTM Method D2281-68.

In one embodiment, this invention provides a composition comprising one or more of any of the trialkylamine oxides of the invention.

In one embodiment, this invention provides a composition comprising at least one amine oxide of the invention wherein trialkylamine oxides other than those of the invention are excluded from the composition.

In one embodiment, this invention provides the composition comprising at least one trialklyamine oxide of the invention comprising at least one nonionic surfactant, anionic surfactant, cationic surfactant, amphoteric surfactant, or combinations thereof.

In one embodiment, this invention provides a composition comprising 0.01% to 30% by weight of at least one trialkylamine oxide of the invention based on the total weight of the composition equaling 100 weight %.

In one embodiment, the invention provides a composition wherein the trialkylamine(s) or trialkylamine mixtures of the invention are used to make the trialkylamine oxide(s) of the invention. In one embodiment, the invention provides a composition comprising at least one trialkyl amine oxide of the invention which does not contain any amine oxides or mixtures of amine oxides other than those described herein as being within the scope of this invention.

In one embodiment, this invention provides a composition comprising at least one trialkylamine oxide of the invention further comprising at least one bleach compound, hydrogen peroxide compound, or combinations thereof.

In one embodiment, this invention provides a composition comprising 1.4 weight % of at least one trialkylamine oxide of the invention, 2.5 weight % NaCl, 4.3 weight % sodium lauryl sulfate, 4.3 weight % sodium lauryl ether sulfate in deionized water wherein said composition has a Brookfield viscosity of less than 4000 centipoise at a shear rate of 3/s.

In one embodiment, this invention provides a composition comprising 1.4 weight % of at least one trialkylamine oxide of the invention (for example, 4-ethyl-N,N-2-trimethyloctan-1-amine oxide), 3.0 weight % NaCl, 4.3 weight % sodium lauryl sulfate, 4.3 weight % sodium lauryl ether sulfate in deionized water wherein said composition has a Brookfield viscosity of less than 3500 centipoise at a shear rate of 3/s.

In one embodiment, this invention provides a composition comprising 1.4 weight % of at least one trialkylamine oxide of the invention (for example, 4-ethyl-N,N-2-trimethyloctan-1-amine oxide), 3.5 weight % NaCl, 4.3 weight % sodium lauryl sulfate, 4.3 weight % sodium lauryl ether sulfate in deionized water wherein said composition has a Brookfield viscosity of less than 2100 centipoise at a shear rate of 3/s.

In one embodiment, this invention provides a composition comprising 1.4 weight % of at least one trialkylamine oxide of the invention (for example, 4-ethyl-N,N-2-trimethyloctan-1-amine oxide), 4.0 weight % NaCl, 4.3 weight % sodium lauryl sulfate, 4.3 weight % sodium lauryl ether sulfate in deionized water wherein said composition has a Brookfield viscosity of less than 1500 or less than 1000 or less than 700 centipoise at a shear rate of 3/s.

In one embodiment, this invention provides home care products, industrial cleaners, agrochemical formulations, coatings, fuel treatments, oil cleaners, oil recovery, oil dispersants, disinfectants, water treatments, bleaches, detergents, stain removers, soaps, oily soil cleaners, grease cutters, soft surface cleaners or hard surface cleaners comprising the composition further comprising any one of the trialkylamine oxides or trialkylamine oxide mixtures of the invention. The trialkylamine oxides or mixtures of trialkyamine oxides of the invention or compositions of the invention can be grease cutters or be present in grease cutters which are effective at oily soils such as sebum, palm or coconut oil, or animal fat.

In one embodiment, this invention provides dish detergents, kitchen surface cleaners, bathroom surface cleaners, upholstery cleaners, laundry stain removers, carpet cleaners, carpet spot removers, or laundry detergents further comprising any one of the trialklylamine oxides or trialkylamine oxide mixtures of the invention.

In one embodiment, this invention provides a laundry detergent comprising any trialkylamine oxide of the invention having at least a 1% or 2% or 3% or 4% or 5% or 6% or 7% or 8% or 9% or 10% or 11% or 12% or 13% or 15% increase in total stain removal index according to ASTM Method D4265, for example, 2% to 11% increase or 3 to 11% increase in total stain removal index according to ASTM Method. The laundry of this embodiment can comprise a commercial laundry liquid comprising ethoxylated lauryl alcohol, sodium laureth sulfate, sodium carbonate, tetrasodium iminosuccinate, acrylic polymer and stilbene disulfonic acid triazine brightener, and can contain no enzymes, dyes or fragrance, for example, the detergent can be ALL FREE CLEAR made by Henkel Corporation, USA.

The present invention includes and expressly contemplates any and all combinations of embodiments, features, characteristics, parameters, and/or ranges disclosed herein. That is, the invention may be defined by any combination of embodiments, features, characteristics, parameters, and/or ranges mentioned herein.

This invention can be further illustrated by the following examples of preferred embodiments thereof, although it will be understood that these examples are included merely for purposes of illustration and are not intended to limit the scope of the invention unless otherwise specifically indicated.

EXAMPLES

For the Examples herein, some of the abbreviations used herein are defined in the following Table and others are throughout the Description and the Examples:

| Abbreviation | Name |
|---|---|
| APG | Alkylpolyglucoside |
| BAC | Benzalkonium chloride |
| CSTR | Continuous stirred tank reactor (CSTR) |
| ELSD | Evaporative light scattering detector |
| EtOH | Ethanol |
| GC-FID | Gas Chromatography-Flame ionization detector |
| GC-MS | Gas Chromatography-Mass spectrometry |
| HEH | 2-Ethylhexanal |
| LABS | Linear alkylbenzene sulfonate |
| LAE10 | Linear alcohol ethoxylate, 10 moles EO average |
| LAO | N,N-dimethyl laurylamine oxide |
| meq/g | Milliequivalents/gram |
| nHBu | n-Butyraldehyde |
| Ru/C | Ruthenium on carbon |
| SLES | Sodium lauryl ether sulfate |
| SLS | Sodium lauryl sulfate |
| SDS | Sodium dodecyl sulfate |
| (TBABr) | Tetrabutyl ammonium bromide |
| Wt | Weight |

Example 1. Synthesis of C11 enal (4-ethyl-2-methyloct-2-enal)

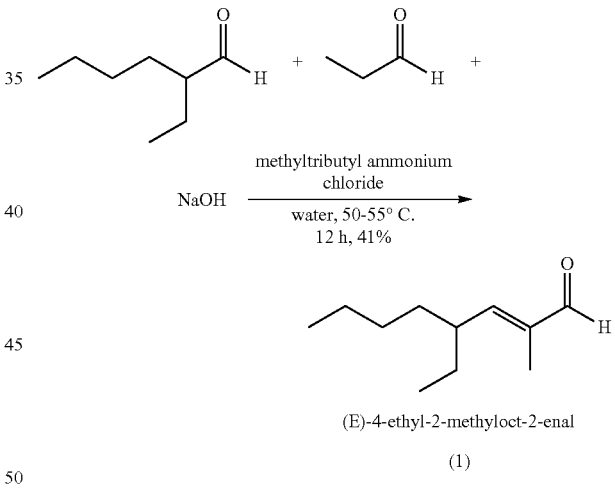

(E)-4-ethyl-2-methyloct-2-enal (1)

To a solution of NaOH (250 g, 3.12 mol) in water (303 mL) was added tributylmethylammonium chloride (49 g, 0.156 mol). To this solution, a premix solution of 2-ethyl hexaldehyde (500 g, 3.90 mol) and propionaldehyde (190 g, 3.28 mol) was added dropwise over the period of 5 h. The addition was maintained such that the temperature of the reaction did not exceed 55° C. The contents of the reaction were stirred at 50° C. for 12 h. The reaction was cooled to room temperature and the contents were transferred to a separatory funnel. The aqueous layer was separated and the organic layer was washed sequentially with water (500 mL), saturated aq. NH$_4$Cl (500 mL) and water (500 mL). The organic layer was separated, dried over MgSO$_4$ and filtered. The pure enal of this Example was distilled at 85° C. (vapour temperature) under 4 mm reduced pressure.

Example 2. Reduction of C11 enal 4-ethyl-2-methyloctanal (C11-aldehyde)

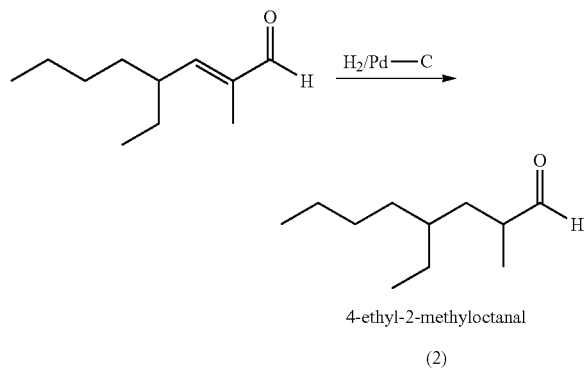

4-ethyl-2-methyloctanal (2)

The C11-enal obtained in Example 1 was hydrogenated using palladium (Pd)—C (1 mol %) under hydrogen pressure (400 psi) at 120° C. The resultant aldehyde in this Example 2, 4-ethyl-2-methyloctanal, was distilled at 80° C.-85° C. (vapor temperature) under 3 mm reduced pressure.

Example 3: Synthesis of 2,4-diethyl-2-octenal

Charge a 3 neck, 1 L (liter) flask with Water (133 ml), sodium hydroxide (56.7 g, 1418 mmol), and tetrabutylammonium chloride (25.0 g, 90 mmol). Using a magnetic stir bar, stir to dissolve. Attach a 500 mL liquid dropping funnel charged with butyraldehyde (75.1 g, 1042 mmol) and 2-ethylhexanal (257.2 g, 2006 mmol). Add the aldehyde mixture to the aqueous mixture in the pot dropwise over 2-3 h. After aldehyde addition is complete, pour the mixture into a 1 L separatory funnel. Separate the aqueous layer and wash the organic layer with brine (1×100 mL) and water (2×100 mL). Separate the organic layer, dry over MgSO$_4$, and filter. The crude reaction mixture (190 g) contains 46% 2-ethylhexanal and 33% 2,4-diethyloct-2-enal. This corresponds to 100% conversion of n-butyraldehyde and 56.9% yield, based on moles of butyraldehyde, of 2,4-diethyloctenal.

Example 4: Synthesis of 2,4-diethyl-2-octenal

Charge a 3 neck, 12 L flack with Water (1596 ml), sodium hydroxide (680.4 g), and tetrabutylammonium bromide (348.12 g). Using a magnetic stir bar, stir to dissolve. Attach 1 L liquid dropping funnel charged with butyraldehyde (901.2 g) and 2-ethylhexanal (3086.4 g). Add the aldehyde mixture to the aqueous mixture dropwise over 2 to 3 h. After aldehyde addition is complete, pour the mixture into a separatory funnel. Separate the aqueous layer and wash the organic layer with brine (300 ml) and water (600 ml). Separate the aqueous layer and wash the organic layer with 5% HCl (200 ml) and water (100 ml). Separate the organic layer, dry over MgSO$_4$, filter, and analyze by gas chromatography. Crude reaction mixture (2278 g) contains 44% 2-ethylhexanal, 1% 2-ethyl-hex-2-enal, 1% 2-ethylhexanol, 2% 2-ethylhexanoic acid, 44% 2,4-diethyl-octenal, and the balance unidentified heavies. This corresponds to 60% yield of 2,4-diethyloctenal.

Example 5: Synthesis of 2,4-diethyl-2-octenal with Benzalkonium Chloride as the Phase Transfer Catalyst (PTC)

Charge a 3 neck, 1 L flask with Water (75 ml), sodium hydroxide (28.3 g, 708 mmol), and benzalkonium chloride (8.84 g, 26 mmol). Using a magnetic stir bar, stir to dissolve. Attach 1 L liquid dropping funnel charged with butyraldehyde (37.5 g, 520 mmol) and 2-ethylhexanal (133.4 g, 1040 mmol). Add the aldehyde mixture to the aqueous mixture dropwise over 2 to 3 h. After aldehyde addition is complete, drain mixture by parts into a 3 L separatory funnel. Separate the aqueous layer and wash the organic layer with brine (50 ml) and water (100 ml). Separate the aqueous layer and wash the organic layer with 5% HCl (50 ml) and water (100 ml). Separate the organic layer, dry over MgSO$_4$, filter, and analyze by gas chromatography. Crude reaction mixture (167.03 g) contains 60% 2-ethylhexanal, 5.5% 2-ethyl-hex-2-enal, 0.5% 2-ethylhexanol, 1.5% 2-ethylhexanoic acid, 17% 2,4-diethyl-octenal, and the balance unidentified heavies. This corresponds to 30% yield of 2,4-diethyl-2-octenal.

Example 6: Synthesis of 2,4-diethyl-2-octenal without PTC

Charge a 3 neck, 1 L flask with water (133 ml), sodium hydroxide (56.7 g, 1418 mmol). Using a magnetic stir bar, stir to dissolve. Attach a 500 mL liquid dropping funnel charged with butyraldehyde (75.1 g, 1042 mmol) and 2-ethylhexanal (257.2 g, 2006 mmol). Add the aldehyde mixture to the aqueous mixture in the pot dropwise over 2-3 h if possible. After aldehyde addition is complete, pour the mixture into a 1 L separatory funnel. Separate the aqueous layer and wash the organic layer with brine (1×100 mL) and water (2×100 mL). Separate the organic layer, dry over MgSO$_4$, filter, and analyze by gas chromatography. Crude reaction mixture contains 75% 2-ethylhexanal, 6.2% 2-ethyl-hex-2-enal, 2.7% 2,4-diethyloct-2-enal, and the balance being unidentified materials with a boiling point higher than that of 2,4-diethyloct-2-enal (heavies). Yield is 3.2%.

Examples 7-12: Synthesis of 2,4-diethyl-2-octenal with Varying PTC

These examples were carried out as described in Example 3 except the concentration of tetrabutyl ammonium bromide (TBABr) was varied relative to n-butyraldehyde (nHBu) as indicated in Table 1. 2HEH=2-ethylhexanal; C12=2,4-diethyloctenal

TABLE 1

| Example Number | TBABr:nHBu | NaOH:nHBu | 2HEH:nHBu | C12 Yield |
|---|---|---|---|---|
| 7 | 0.09 | 1.4 | 2.0 | 60% |
| 8 | 0.07 | 1.4 | 2.0 | 60% |
| 9 | 0.05 | 1.4 | 2.0 | 60% |
| 10 | 0.04 | 1.4 | 2.0 | 40% |
| 11 | 0.03 | 1.4 | 2.0 | 20% |
| 12 | 0.02 | 1.4 | 2.0 | 38% |

Examples 13-16: Synthesis of 2,4-diethyl-2-octenal with Varying NaOH Equivalents These examples were carried out according to the procedure outlined in Examples 13-16 except the equivalents of NaOH relative to n-butyraldehyde (nHBu) were varied as shown in Table 2. The data in Table 2 demonstrates that using a ratio of 1.15 to 1.25 of NaOH:nHbu provides a enal yield of at least 40%.

TABLE 2

| Example Number | Mmol nHBu | Mmol NaOH | NaOH:nHBu | C12 Yield |
|---|---|---|---|---|
| 13 | 520 | 650 | 1.25 | 41% |
| 14 | 520 | 598 | 1.15 | 42% |
| 15 | 520 | 520 | 1.00 | 33% |
| 16 | 520 | 260 | 0.5 | 28% |

Examples 17-24: Continuous Synthesis of 2,4-diethyl-2-octenal

A jacketed 3 L glass round bottom with four necks and a bottom drain containing a stop cock, was used as a continuous stirred tank reactor. The center neck was fitted with an overhead stirrer controlled by an electric motor. The left neck was fitted with a Claisen tube to which are connected two veritcally mounted 2 L glass feed tanks. Each feed tank was attached to a 0-20 mL Eldex brand liquid feed pump. The drain was connected to the intake of a high speed circulating pump. The discharge of the pump passes through an inline static mixer and returns to the CSTR through the right neck. A slip stream of product was removed on the downstream side of the static mixer through a 0-40 mL Eldex pump and into another vertically mounted 2 L glass tank that serves as a decanter. The fourth neck of the CSTR contains a J-type thermocouple connected to a JKEM type temperature indicator. Heating was provided by a circulating bath containing a 50/50 mixture of water and ethylene glycol. The heating medium was circulated through the glass jacket on the reactor to keep the reactor mixture at the desired temperature.

In a typical aldol experiment, one glass feed tank was filled with a 20% solution of NaOH and the other feed tank was filled with a mixture of 60% HEH, 35% nHBu, and 5% BAC. The reactor was charged with 1500 mL of a 2:1 mixture of crude material and NaOH solution. The contents were stirred at 250 rpm and heated to 55° C. The circulating pump was started and material was moved through the static mixer and returned to the CSTR. When the target temperature was reached, the organic feed pump was begun at 15.0 mL/min and the caustic feed pump was begun at 6.0 mL/min. The product takeoff pump was begun at 21.0 mL/min. Under these conditions, the residence time in the reactor was approximately 60 minutes. One hour after startup the product decanter was emptied and this material discarded. After this time, samples were collected every hour. The bottom aqueous material was decanted from the product tank and weighed. The upper organic layer was decanted, weighed, and analyzed by gas chromatography. The crude organic was retained for distillation. After 7 hours, the experiment was discontinued. In this way, approximately 3 L of crude organic was obtained daily.

Distillation of the decanted, crude organic material was conducted on a 2″ glass Oldershaw column. The column stands 10 feet tall and was approximately 24 trays. The column is attached to a 3 L three neck glass round bottom at the bottom and an overhead chilled glycol condenser. The top tray of the column was topped by a "swinging gate" style takeoff controller with a reflux control magnet attached to an electric timer. The disillate from the swinging gate passes through a second glycol chilled condenser before collecting in a glass fraction cutter. The entire column was maintained under 100 torr vacuum by a Welch type vacuum pump. A similar 1″ Oldershaw column was used employing 30 glass trays. Material was fed constantly into the column from a 4 L glass feed tank. The feed rate was controlled by a bellows type pump and passed through a pre-heater set to 120° C. The basepot overflow was removed through a glass sample thief attached to a glycol chilled condenser. A stainless steel solenoid valve and stainless steel needle valve were used to control the rate of overflow. The solenoid was controlled by an electric timer and the overflow product tank was held at 15 torr.

Organic samples were studied by gas chromatography on an Agilent 6890N. The aqueous samples were run on a Restek RTX-1 fused silica catalog #10126 column (length 60 m, diameter 250 um, film 0.25 um) analyzed by a flame ionization detector (GC-FID). The configuration settings were as follows. Heat the oven to 50° C. initially and hold for 3 minutes, ramp the temperature to 125° C. at 12° C./minute, and hold there for 3 minutes. Next, increase the temperature up 7° C./min to a temperature of 165° C. Then, increase the temperature up 15° C./min to a final temperature of 240° C. The detector setting was held at 300° C. Table 3 shows the yield of C12 enal obtained from a continuous process, changing the ratio of reactants, PTC loading, residence time and temperature.

TABLE 3

3L CSTR results at 2:1 HEH:nHBu ethyl-hex-2-enal

| Example Number | OH:C4 | PTC:C4 | Residence Time (min) | Temperature (° C.) | Butyraldehyde Conversion | C12 Yield (Based on mols of butyraldehyde fed) |
|---|---|---|---|---|---|---|
| 17 | 1.41 | 0.05 | 60 | 53.1 | 97.4% | 50.1% |
| 18 | 1.46 | 0.05 | 110 | 54.2 | 93.1% | 60.8% |
| 19 | 1.49 | 0.05 | 110 | 62.6 | 93.2% | 57.6% |
| 20 | 1.23 | 0.05 | 60 | 57.1 | 84.5% | 43.6% |
| 21 | 1.10 | 0.05 | 60 | 56.9 | 88.6% | 50.1% |
| 22 | 1.04 | 0.05 | 60 | 56.9 | 89.3% | 55.8% |
| 23 | 1.17 | 0.03 | 60 | 55.0 | 87.9% | 41.2% |
| 24 | 1.51 | 0.05 | 60 | 70.5 | 98.6% | 51.9% |

Example 25: Hydrogenation of 2,4-diethyl-2-octenal

A 2 L Hastelloy Autoclave Engineers autoclave is charged with 400 g of purified 2,4-diethyl-2-octenal and 400 g of dry isopropanol. 10.0 g of 0.75% Pd on Al2O3 support is added to a steel mesh catalyst basket. The basket is attached to the stirring shaft of the autoclave above the impeller. The autoclave is sealed and purged with hydrogen gas. The autoclave is brought to 345 kPa with H2 and heated to 150°

C. The autoclave is then brought 6895 kPa with H2. Using a gas reservoir system, the autoclave pressure is maintained for 6 h. After 6 h, the autoclave is cooled and vented. The reaction consumed 5.4 Gmol of hydrogen. The crude reaction mixture (782 g) contains 50% isopropanol, 45% 2,4-diethyloctanal, 2.37% 2,4-diethyloctenal, 7.7% 2,4-diethyloctanol, and 3.5% 2,4-diethyl-oct-2-en-1-ol. This corresponds to 98% conversion and 77% yield of 2,4-diethyloctenal.

Examples 26-28: Hydrogenation of 2,4-diethyl-2-octenal

Synthesis of 2,4-diethyl-2-octanal was carried out in the same manner as Example 25 above except the hydrogen pressure was varied as indicated in Table 4.

TABLE 4

| Example Number | Pressure (kPa) | Enal Conversion | 2,4-diethyloctanal Yield |
| --- | --- | --- | --- |
| 26 | 6895 | 98% | 77% |
| 27 | 5171 | 66% | 54% |
| 28 | 3447 | 60% | 55% |

Examples 29-32: Catalyst Comparison

A series of catalysts of differing Pd loading and supports, obtained from Evonik Corporation, were tested in the following manner: A 300 mL stainless steel Autoclave Engineers autoclave is charged with 50 g of purified 2,4-diethyl-2-octenal and 50 g of dry isopropanol. 5.0 g of catalyst obtained from Evonik is added to a steel mesh catalyst basket. The basket is attached to the stirring shaft of the autoclave above the impeller. The autoclave is sealed and purged with hydrogen gas. The autoclave is brought to 345 kPa with H2 and heated to 150° C. The autoclave is then brought 6895 kPa with H2. Using a gas reservoir system, the autoclave pressure is maintained for 4 h. After 4 h, the autoclave is cooled and vented. The results are presented in Table 5.

TABLE 5

| Example Number | Catalyst | Pd Loading | Support | Conversion | Yield |
| --- | --- | --- | --- | --- | --- |
| 29 | Noblyst 1512 | 0.7% | Carbon | 92% | 80% |
| 30 | Noblyst 1006 | 1.0% | Carbon | 91% | 80% |
| 31 | Noblyst 1005 | 2.0% | Silica | 44% | 33% |
| 32 | E 105 O/W | 5.0% | Carbon | 62% | 42% |

Example 33: Hydrogenation of 2,4-diethyl-2-octenal with Ru

A 300 mL stainless steel Autoclave Engineers autoclave is charged with 50 g of purified 2,4-diethyl-2-octenal and 50 g of dry isopropanol. 5.0 g of 3% Run on 2 mm carbon extract support obtained from Johnson-Matthey is added to a steel mesh catalyst basket. The basket is attached to the stirring shaft of the autoclave above the impeller. The autoclave is sealed and purged with hydrogen gas. The autoclave is brought to 345 kPa with H2 and heated to 150° C. The autoclave is then brought 6895 kPa with H2. Using a gas reservoir system, the autoclave pressure is maintained for 4 h. After 4 h, the autoclave is cooled and vented. The reaction consumed 0.8 Gmol of hydrogen. The crude reaction mixture (85 g) contains 30% isopropanol, 12% 2-ethylhexanol, 3.4% 2,4-diethyloctanal, 14% 2,4-diethyloctenal, 18% 2,4-diethyloctanol, and 21% 2,4-diethyl-oct-2-en-1-ol. This corresponds to 76% conversion and 7% yield of 2,4-diethyloctenal Example 34: Biodegradability—OECD 301B The biodegradability of the branched aldehyde intermediates of Example 2 (4-ethyl-2-methyloctanal) and Example 25 (2,4-diethyl-2-octenal) were determined by the Ready Biodegradability —CO2 Evolution Test-Degradation of test compound according to OECD Guidelines for Testing of Chemicals $CO_2$ Evolution Test 301B.

TABLE 6

| | Biodegradation (%) | | |
| --- | --- | --- | --- |
| Days | sodium acetate control | $C_{11}$ aldehyde Example 2 | $C_{12}$ aldehyde Example 25 |
| 0 | 0 | 0 | 0 |
| 2 | 32 | 0 | 0 |
| 6 | 52 | 15 | 0 |
| 7 | 54 | 21 | 9 |
| 9 | 60 | 31 | 27 |
| 14 | 66 | 47 | 48 |
| 19 | 69 | 54 | 53 |
| 23 | 71 | 56 | 53 |
| 28 | 72 | 57 | 55 |
| 29 | 74 | 57 | 55 |
| 29 | 78 | 61 | 57 |

Example 35. Conversion of C11 aldehyde to 4-ethyl-N,N,2-trimethyloctan-1-amine (3) (C11-amine)

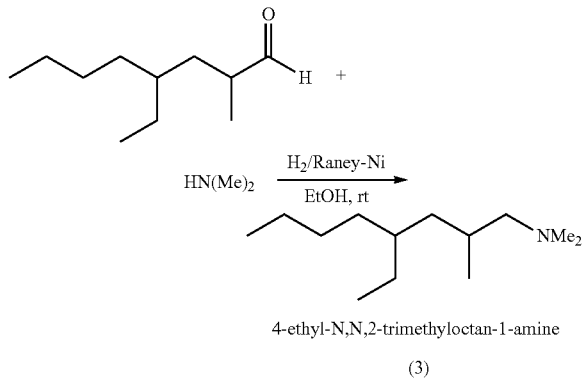

4-ethyl-N,N,2-trimethyloctan-1-amine (3)

To a 500 mL thick-walled parr-shaker flask, Raney-Ni (2 g) was added. A solution of dimethylamine (11% solution in EtOH, 193 g, 470 mmol) was added to this flask. To this solution was then added $C_{11}$-aldehyde (2) (20 g, 117 mmol) obtained in the last step and the contents were hydrogenated using H2 gas (30 psi) for 12 h. After the reaction was complete, the catalyst was filtered and the volatiles were evaporated under reduced pressure. The residue was diluted with EtOAc (200 mL) and 10% aq. HCl (200 mL). The organic layer was separated and the product aq. Layer was washed with additional EtOAc (200 mL). The aq. Layer was separated and basified using saturated aq. $NaHCO_3$ solution. This solution was then transferred to a separatory funnel and the pure product extracted using EtOAc (3×300 mL). The organic layer was separated, dried over $MgSO_4$ and concentrated under reduced pressure to afford the pure $C_{11}$ amine (3).

Example 36: Synthesis of 4-ethyl, 2-methyl, N,N-dimethylhexan-1-amine Via 4-ethyl, 2-methyloctanal

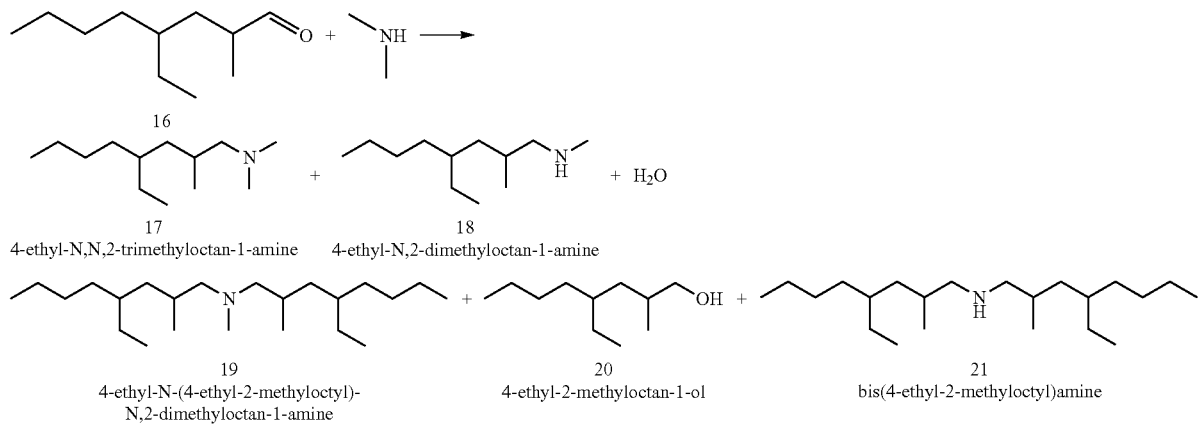

A vertical fixed bed reactor was charged with 50 ml (50 g) of a tableted $CuO/ZnO/Al_2O_3$ catalyst. After activation with hydrogen (180° C., ambient pressure, 24 h) a continuous gaseous flow was fed to the reactor which consist of hydrogen, dimethylamine and 4-ethyl, 2-methyloctanal (16) in the reactor at a pressure of 10 barg and a temperature of 250° C. The ratio of dimethylamine to the aldehyde to hydrogen was set at 3/1/50 and the aldehyde feed was set at 0.15 g/g catalyst/h. Bypass high pressure samples were taken from the reaction mixture downstream of the reactor and analyzed by gas chromatography. The experiments were run for 100 h and at steady state, the conversion was 99.9% and the yield towards the wanted 4-ethyl, 2-methyl, N,N-dimethylhexan-1-amine (17) was 85.04%. Yields of the different side-products (4-ethyl, 2-methylhexanol (20); 4-ethyl, 4-ethyl,2-methyl, N-methylhexan-1-amine (18); N-(4-ethyl, 2-methyl hexyl)-N-methylhexan-1-amine (19) and bis (4-ethyl, 2-ethyl hexyl)amine) were respectively 0.36%, 8.15%, 1.63% and 0.18%.

Example 37: Synthesis of 2,4-diethyl, N,N-dimethyloctan-1-amine via 2,4-diethyl-2-octenal

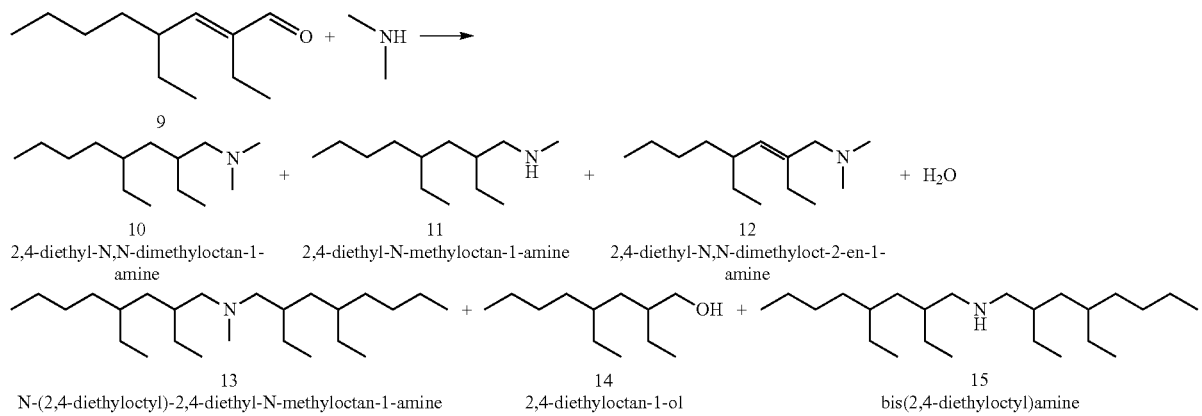

A vertical fixed bed reactor was charged with 50 ml (50 g) of a tableted CuO/ZnO/Al catalyst. After activation with hydrogen (180° C., ambient pressure, 24 h) a continuous gaseous flow was fed to the reactor which consist of hydrogen, dimethylamine and 2,4-diethyl-2-octenal (9) in the reactor at a pressure of 10 barg and a temperature of 250° C.

The ratio of dimethylamine to the aldehyde to hydrogen was set at 3/1/50 and the aldehyde feed was set at 0.15 g aldehyde/g catalyst/hour. Bypass high pressure samples were taken from the reaction mixture downstream of the reactor and analyzed by gas chromatography. The experiments were run for 100 h and at steady state, the conversion was 99.9% and the yield towards the desired 2,4-diethyl, N,N-dimethyloctan-1-amine was 71.5%. Yields of the different side products 2,4-diethyloctanol; 2,4-diethyl, N-methyloctan-1-amine; 2,4-diethyl,N,N-dimethyloct-2-en-1-amine; N-(2,4-diethyloctyl)-N-methyloctan-1-amine and bis(2,4-diethyloctyl)amine) were respectively 2.13%, 5.20%, 11.14%, 3.20% and 1.25%.

Example 38: Synthesis of Branched BAC-b12 (N-benzyl-2,4-diethyl-N,N-dimethyloctan-1-aminium chloride)

2,4-Diethyl N,N-dimethyloctylamine (3.00 g; 14.06 mmol) and benzyl chloride (1.78 g; 14.06 mmol; 1.0 equiv) were combined in a 40 mL vial with a magnetic stir bar, which was heated with stirring in a 77° C. heat block for 6 h, at which point the mixture had solidified. Water (1.59 g) was added, and the mixture was stirred with heating at 77° C. for an additional 6 h to afford 99.3% conversion of the amine to branched BAC-b12 according to HPLC analysis. The resulting mixture is ca. 75% branched BAC-12 in water as a homogeneous liquid.

1H NMR (DMSO-d6): δ7.7-7.4 (m, 5H); 4.65 (m, 2H); 3.44 (m), 1H); 3.15 (t, J=11.7 Hz); 3.0-2.9 (m, 6H); 1.55-1.05 (m, 14H); 0.95-0.7 (m, 9H).

HPLC (150×4.6 mm Zorbax SB-C8 column, 75:25 (v:v) methanol:water (containing 0.1% trifluoroacetic acid) for 10 min, gradient to 100% methanol over 1 min, held at 100% methanol for 9 min, ELSD detection detection): tR 3.6 min. (starting amine); 4.1 min (branched BAC-b12).

Example 39: Synthesis of Branched C12 Enal with (Branched BAC as PTC), NaOH, PTC, C4+C8

A 100 mL three neck round bottom flask is charged with 7.77 g (194 mmol) of NaOH pellets. 30 mL of water is added and the mixture stirred by means of a magnetic stir bar until the NaOH is dissolved. 3.14 g of a 75 weight % aqueous solution of N-benzyl-2,4-diethyl-N,N-dimethyloctan-1-aminium chloride is added and stirring continues. A 50 mL dropping funnel, glycol chilled condenser, and thermometer are attached to the round bottom. The entire apparatus is brought to 50° C. The dropping funnel is charged with a mixture of n-butyraldehyde (10 g, 139 mmol) and 2-ethylhexanal (35.6 g, 277 mmol) and the aldehyde mixture is added slowly dropwise to the caustic mixture. After three hours, the mixture is cooled and poured into a 125 mL separatory funnel. The bottom aqueous layer is separated. The upper organic phase is washed with water and brine. The organic layer is dried over MgSO$_4$, filtered, and the filtrate analyzed by GC. GC analysis shows 51% yield of 2,4-diethyl-oct-2-enal.

Example 40: Synthesis of Branched C12 Enal with (Branched BAC as PTC)

A 100 mL three neck round bottom flask is charged with 7.77 g (194 mmol) of NaOH pellets. 30 mL of water is added and the mixture stirred by means of a magnetic stir bar until the NaOH is dissolved. 3.14 g of a 75 weight % aqueous solution of N-benzyl-2,4-diethyl-N,N-dimethyloctan-1-aminium chloride is added and stirring continues. 2-ethylhexanal (35.6 g, 277 mmol) is added. A 50 mL dropping funnel, glycol chilled condenser, and thermometer are attached to the round bottom. The entire apparatus is brought to 50° C. The dropping funnel is charged with of n-butyraldehyde (10 g, 139 mmol) and the aldehyde mixture is added slowly dropwise to the caustic mixture. After three hours, the mixture is cooled and poured into a 125 mL separatory funnel. The bottom aqueous layer is separated. The upper organic phase is washed with water and brine. The organic layer is dried over MgSO$_4$, filtered, and the filtrate analyzed by GC. GC analysis shows 52% yield of 2,4-diethyl-oct-2-enal.

Example 41: Synthesis of Branched C12 Butyl Quat

To a 25 mL sealed flask was added 2,4-diethyl-N,N-dimethyloctan-1-amine (3.0 g, 14.06 mmol) and 1-bromobutane 1.51 mL, 14.06 mmol). The tube was sealed tightly using a Teflon screw cap and placed in a preheated oil bath at 120° C. A blast shield was placed in front of the reaction. The contents of the tube was stirred at 120° C. for 12 h. The reaction tube was removed from the oil bath and allowed to cool to room temperature. 1H-NMR of the crude reaction mixture shows complete conversion of C12-dimethyl amine to N-butyl-2,4-diethyl-N,N-dimethyloctan-1-aminium bromide (branched 012-butyl quat). The reaction mixture was diluted with water to make the final concentration to 75%.

1H NMR (500 MHz, CDCl3)) δ3.75-3.47 (m, 6H), 3.47-3.32 (m, 12H), 3.17 (ddd, J=13.4, 9.2, 3.9 Hz, 2H), 1.91-1.62 (m, 6H), 1.52 (tq, J=7.1, 3.1 Hz, 4H), 1.48-1.07 (m, 28H), 1.05-0.73 (m, 29H) ppm. $^{13}$C NMR (126 MHz, CDCl3) 568.84, 68.77, 64.45, 51.42, 51.07, 37.89, 37.86, 36.06, 35.94, 35.90, 32.85, 32.38, 31.69, 31.63, 28.78, 28.61, 25.99, 25.96, 25.77, 25.25, 24.86, 23.11, 23.07, 19.64, 14.15, 14.11, 13.76, 10.73, 10.67, 10.46, 10.01, 9.94 ppm

Example 42: Synthesis of C12-enal using N-butyl-2,4-diethyl-N,N-dimethyloctan-1-aminium bromide (Branched C12-butyl quat.) as PTC To a 100 mL 3-neck flask equipped with a stir bar, reflux condenser, addition funnel and a temperature probe, NaOH (10.0 g, 125 mmol, 50% solution in wa), water (12.16 mL) and N-butyl-2,4-diethyl-N,N-dimethyloctan-1-aminium bromide (2.92 g, 6.25 mmol, 75% solution in water) prepared in the last step was added. The flask was placed in an oil bath and the contents were stirred at 50° C. A mixture of 2-ethyl hexaldehyde (24.37 mL, 156 mmol) and n-butyraldehyde (11.83 mL, 131 mmol) was charged in a separatory funnel and added to the stirred mixture dropwise. The addition was maintained at such a rate that the internal temperature of the reaction did not rise above 55° C. After the addition was complete, the heating was continued for overnight and the crude reaction mixture was analyzed by GC which showed 38.9% (area %) of C12-enal.

Comparative Example

To a 100 mL 3-neck flask equipped with a stir bar, reflux condenser, addition funnel and a temperature probe, NaOH (10.0 g, 125 mmol, 50% solution in water), water (12.16 mL) and methyl-tributyl ammonium chloride (1.96 g, 6.25 mmol, 75% solution in water) was added. The flask was placed in an oil bath and the contents were stirred at 50° C. A mixture of 2-ethyl hexaldehyde (24.37 mL, 156 mmol)

and n-butyraldehyde (11.83 mL, 131 mmol) was charged in a separatory funnel and added to the stirred mixture dropwise. The addition was maintained at such a rate that the internal temperature of the reaction did not rise above 55° C. After the addition was complete, the heating was continued for overnight and the crude reaction mixture was analyzed by GC which showed 44.7% (area %) of C12-enal.

Example 43: Synthesis of 4-ethyl-N,N-2-trimethyl-octan-1-amine oxide (4) (Branched C11-amine oxide)

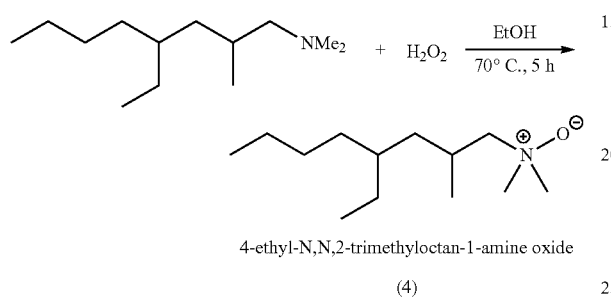

4-ethyl-N,N,2-trimethyloctan-1-amine oxide (4)

To a solution of C11-amine, 4-ethyl-N,N,2-trimethyloctan-1-amine (25 g, 125 mmol) in EtOH (125 mL) was added hydrogen peroxide (30% solution in water, 42.6 g, 376 mmol). The contents of the flask were stirred at 70° C. for 5 h. After the reaction was complete, the excess peroxide was quenched with activated charcoal (negative peroxide strip test). The contents of the flask were filtered through a 1 mm filter cloth. The filter cloth was washed with additional EtOH (200 mL). The combined filtrates were concentrated to dryness under reduced pressure. Residual EtOH and water was removed using nitrogen purge. The removal of any residual solvent using heat was avoided as the material caused decomposition through Cope-elimination at higher temperature.

Example 44: Synthesis of 2,4-diethyl-N,N-dimethyloctan-1-amine oxide (Branched C12-amine oxide)

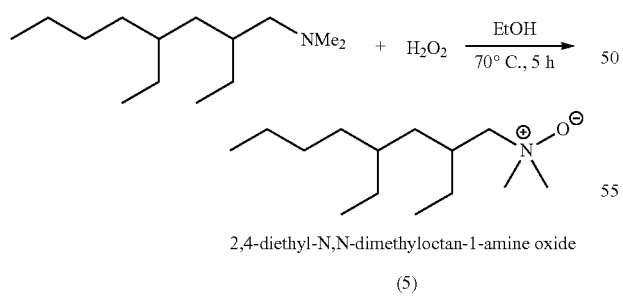

2,4-diethyl-N,N-dimethyloctan-1-amine oxide (5)

To a solution of C12-amine, 2,4-diethyl, N,N-dimethyloctan-1-amine (50 g, 234 mmol) in EtOH (234 mL) was added hydrogen peroxide (30% solution in water, 80 g, 703 mmol). The contents of the flask were stirred at 70° C. for 8 h. After the reaction was complete, the excess peroxide was quenched with activated charcoal (negative peroxide strip test). The contents of the flask were filtered through a 1 mm filter cloth. The filter cloth was washed with additional EtOH (300 mL). The combined filtrates were concentrated under reduced pressure. The residual EtOH and water was removed using nitrogen purge. The removal of any residual solvent using heat was avoided as the material caused decomposition through Cope-elimination at higher temperature).

Example 45: Modified Procedure for Synthesis of 2,4-diethyl-N,N-dimethyloctan-1-amine oxide (Branched C12-amine oxide)

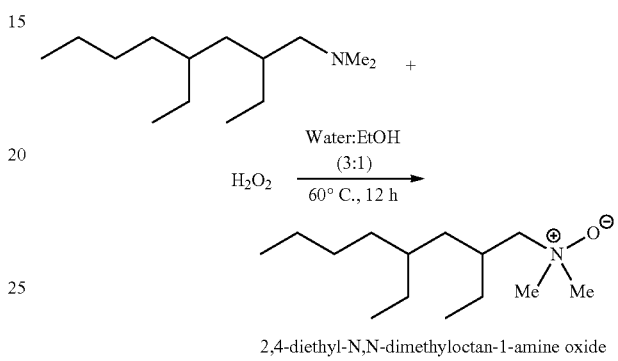

2,4-diethyl-N,N-dimethyloctan-1-amine oxide

To a 500 mL 3-neck round bottom flask equipped with a stir bar, reflux condenser and a thermocouple, was added C12-amine, 2,4-diethyl, N,N-dimethyloctan-1-amine (50 g, 234 mmol), EtOH (58 mL) and water (150 mL). The mixture was stirred at 60° C. and hydrogen peroxide (34.5 g, 305 mmol, 30% solution in water) was added to it dropwise. The addition was maintained such that the internal temperature did not exceed 60-63° C. (~30 minutes). The contents of the flask were stirred at 60° C. for 12 h. After the reaction was complete (as evidenced by HNMR), the excess hydrogen peroxide was quenched with activated charcoal (negative peroxide strip test). The contents of the flask were filtered through a 1 mm filter cloth. The filter bed was washed thoroughly with water in several small portions to ensure complete filtration of the C12-amine oxide. The combined filtrates were concentrated under reduced pressure. The EtOH removal was monitored by HNMR. If necessary, additional water was added to the flask to aid the removal of EtOH. After EtOH was removed completely from the reaction mixture, the final weight of the amine oxide was adjusted to 30% by additional water.

Example 46: Surface Wetting—Draves Wet Out Time

The surface wetting ability of the amine oxides with linear and branched hydrophobes from Examples 43 to 45 were compared using the Draves Wetting Test (ASTM D2281-68). A 0.05 wt % (actives basis) solution of amine oxide in deionized (DI) water was used to determine the Draves wet-out time (WOT) in seconds. 0.75 g of surfactant was dispersed in 1,500 ml of DI water. The wet-out time (WOT) in seconds is recorded in Table 7 (average of 3 measurements). LAO is Lauramine oxide (linear hydrophobe), Sigma catalog number 40236. The results are shown in Table 7.

TABLE 7

|  | Wet out time |
| --- | --- |
| Linear LAO | 33 sec |
| Oxo C11 AO 4-ethyl-N,N-2-trimethyloctan-1-amine oxide Example 44 | >300 sec |
| Oxo C12 AO 2,4-diethyl-N,N-dimethyloctan-1-amine oxide Example 44 | >300 sec |

Example 47: Foam Height: High Shear

The surface foam volume and persistence of the amine oxides with linear and branched hydrophobes from Examples 43 and 44 were compared. A 0.05 wt % (actives basis) solution of the test surfactant was made in deionized water. 250 ml of the test solution was added the beaker of a Waring blender, capped, and then blended on High for 30 seconds and immediately transferred to a 1 L graduated cylinder. The total volume of foam plus liquid, as well as the liquid layer alone was recorded. The foam and liquid volumes were recorded again after 5 minutes. The foam volume only (excluding the liquid volume) is reported in Table 8.

TABLE 8

|  | Foam volume (ml) Initial | Foam volume (ml) 5 min | % decrease |
| --- | --- | --- | --- |
| Linear LAO | 523 | 500 | 4% |
| Oxo C11 AO (4-ethyl-N,N-2-trimethyloctan-1-amine oxide Example 43) | 267 | 0 | 100% |
| Oxo C12 AO (2,4-diethyl-N,N-dimethyloctan-1-amine oxide Example 44) | 370 | 0 | 100% |

Example 48: Salt Thickening

Amine oxides with linear and branched hydrophobes from Examples 43 to 44 were compared for salt-thickening in a formulation. Linear amine oxides tend to increase the viscosity of a formulation containing NaCl in a dose-dependent manner. The viscosity (cP; shear rate 3/s) of a simple formulation was measured as the salt concentration varied from 0 to 5 wt %.

TABLE 9

| Ingredient | Content |
| --- | --- |
| SLS | 4.3% |
| SLES | 4.3% |
| Amine oxide | 1.4% |
| NaCl | As noted |
| DI water | q.s. |

TABLE 10

| NaCl content wt % | Viscosity with LAO | Viscosity with C11 AO (4-ethyl-N,N-2-trimethyloctan-1-amine oxide Example 43) |
| --- | --- | --- |
| 0 | 2 | 2 |
| 0.5 | 2 | 7 |
| 1.0 | 11 | 36 |
| 1.5 | 115 | 257 |
| 2.0 | 1,494 | 2,050 |
| 2.5 | 7,562 | 3,635 |
| 3.0 | 17,343 | 3,459 |
| 3.5 | 25,302 | 2,021 |
| 4.0 | 27,585 | 670 |
| 4.5 | 24,918 | 288 |
| 5.0 | 19,368 | 148 |

Example 49: Mildness Predicted by Zein Solubilization Test

Amine oxides with linear and branched hydrophobes from Examples 43 and 44 were compared in a screen to predict mildness of surfactants. There is a correlation between the ability of a surfactant to denature a protein and the skin irritation potential of that surfactant. The relationship is believed to result from surfactant binding to proteins like keratin, followed by the denaturation of these proteins, leading to skin irritation. A common screening test involves measuring the amount of zein (a corn protein which is insoluble in water) solubilized by a surfactant solution, the Zein Solubilization Test (Moore et al., 2003 and references therein)

For the test, 0.0750 g of zein protein is transferred into a 1.5 mL centrifuge tube. To this 1.5 mL of 1% surfactant solution is added, mixed, and placed in a 30 C incubator with mild stirring for 30 minutes. After 30 minutes has elapsed, the tube is centrifuged for 30 min at 3600 rpm. The solution is filtered through a pre-weighed 8 micron filter paper, and then dried overnight in a 50° C. oven. The insoluble zein residue is then weighed and the wt % Zein dissolved is calculated using the equation below. Each solution is analyzed in triplicate. The Zein score is normalized to a standard included in each set of tests, in this case LAE10; (% zein dissolved=(total zein added−total zein after drying÷Total zein added)×100).

TABLE 11

| Sample | Zein score - normalized to LAE10 |
| --- | --- |
| oxoC12 amine oxide, (2,4-diethyl-N,N-dimethyloctan-1-amine oxide, Example 44) | 0.018 |
| APG, alkylpolyglucoside | 0.586 |
| LAE10, Linear alcohol ethoxylate, EO10 | 1.000 |
| SDS, sodium dodecyl sulfate | 2.470 |
| SLES, sodium lauryl ether sulfate | 3.488 |
| LAO, N,N-dimethyl laurylamine oxide | 4.212 |

TABLE 11-continued

| Sample | Zein score - normalized to LAE10 |
|---|---|
| LABS, linear alkylbenzene sulfonate | 4.670 |

Example 50: Stain Removal in Cold Water

Amine oxides with linear and branched hydrophobes were compared in a screen for stain removal in cold water. Simple laundry liquid formulations were made that included only surfactants and builder. The results are shown in Table 12.

TABLE 12

| Component | Wt % |
|---|---|
| NaCitrate | 1.55 |
| Anionic Steol CS-230 SLES | 6 |
| Anionic Biosoft S-101 LABS | 6 |
| Nonionic Biosoft EC-690 LAE7 | 12 |
| De-ionized water | q.s. |

Standard stain swatches were purchased from Testfabrics, Inc. (West Pittston, Pa.). STC/CFT PC-S-216 is diluted red lipstick on poly/cotton (65/35), and STC/CFT PC-S-132 is high discriminative sebum (synthetic) with pigment on poly/cotton, both made by Center for Testmaterials BV (CFT; The Netherlands). The swatches were pre-cut into 2 inch squares. The test formulation was diluted with DI water to 0.06% total surfactant to make the wash solution. Additives were added at a final concentration of 0.05% active in the wash solution. Stained fabric swatches were added to the wash solution, washed and rinsed at 20° C., and air-dried. The average swatch brightness (L*) for each treatment, and standard deviation, are reported for 3 replicates. A different lower-case letter in the last column indicates treatments that are significantly different from each other (p<0.02). All treatments are brighter than the untreated stain swatches. The nonionics NPE and LAE7 removed the lipstick and sebum stains to the same brightness. Three additives included at 0.05% in a base formulation containing 12% LAE7 significantly improved the removal of the lipstick stain, but not the synthetic sebum stain. Standard (auramine oxide (Sigma LAO) at 0.05% active resulted in a significantly brighter swatch after washing. An amine oxide made from a branched $C_{11}$ aldehyde (branched $C_{11}$ AO) was better than LAO at removing the lipstick stain, and created very little foam in the wash solution compared to LAO.

TABLE 13

| Stain removal estimated by brightness (L*) | | | | | |
|---|---|---|---|---|---|
| | Red lipstick CFT PC-S-216 | | Sebum CFT PC-S-132 | | |
| | avg L* | Std dev | | avg L* | Std dev | |
| No Treatment | 70.3 | 0.58 | a | 71.2 | 1.4 | a |
| 12% LAE7 | 73.9 | 0.57 | b | 72.5 | 1.1 | b |
| 12% LAE7 + Sigma LAO | 74.8 | 0.46 | c | 72.8 | 1.1 | b |

TABLE 13-continued

| Stain removal estimated by brightness (L*) | | | | | |
|---|---|---|---|---|---|
| | Red lipstick CFT PC-S-216 | | Sebum CFT PC-S-132 | | |
| | avg L* | Std dev | | avg L* | Std dev | |
| 12% LAE7 + Branched C11 AO, (4-ethyl-N,N-2-trimethyloctan-1-amine oxide, Example 43) | 76.3 | 0.48 | d | 72.7 | 1.2 | b |

Example 51: ASTM D4265 for Stain Removal in Cold Water (Branched C12 AO)

Amine oxides with linear and branched hydrophobes were compared in a washing machine test for stain removal in cold water. ASTM 4265 is a Standard Guide for Evaluating Stain Removal Performance in Home Laundering. A commercial laundry liquid was used as the base formulation. The commercial laundry liquid (all free clear) contains ethoxylated lauryl alcohol, sodium laureth sulfate, sodium carbonate, tetrasodium iminosuccinate, acrylic polymer and stilbene disulfonic acid triazine brightener, but no enzymes, dyes or fragrance. The base formulation was tested alone or augmented with 2% (volume, actives basis) amine oxide.

The test laundry formulations are evaluated in three separate loads in a household front-loading high-efficiency (HE) washing machine connected to a city water source. The cold water wash option was selected on the machine. The water temperature was monitored using an in-wash recording device, and stayed between 15 and 20° C. for the duration of the test period. Each load contained a pre-stained fabric swatch and clean ballast fabric. The manufacturer-recommended laundry liquid dose was 44 ml/load.

The stain/fabric combination used for this test is the standard SwissaTest EMPA 102; a pre-soiled Cotton-Jersey (23×19 cm) with 15 different stains (3 cm): Make-up, curry, red wine, tomato sauce, blood, chocolate dessert, peat, tea, beta-carotene, grass, animal fat/red dye, baby food, clay, butter and used engine oil. These swatches are available from TestFabrics, Inc., West Pittston Pa.

The test swatches are treated with the products being compared, and the relative degree of stain removal is assessed instrumentally. The stain removal index (SRI) is calculated for each stain type, and the total SRI across all 15 stains is reported. A higher SRI indicates better stain removal. The duration of the cycle is also noted. When LAO was added at 2%, the oversuds error was activated in the machine, and the rinse cycle continued indefinitely, or else the cycle aborted.

TABLE 14

| Laundry Liquid | Total SRI | Duration of full cycle (min) |
|---|---|---|
| Base formulation | 508 | 48 |
| Base + 1% oxoC12 AO (2,4-diethyl-N,N-dimethyloctan-1-amine oxide, Example 44) | 524 | 46 |
| Base + 2% oxoC12 AO of Example 44 | 564 | 47 |
| Base + 2% LAO | No data | Suds Error |

Example 52: Stain Removal of Branched C12 Amine Oxide Added to a High Anionic Laundry Liquid A high-anionic surfactant laundry liquid formula was made and diluted for use to a final surfactant concentration of 0.06% in the wash solution.

TABLE 15

| Ingredient | "Lab Liquid A" |
|---|---|
| AES, alkyl ether sulfate, Steol CS-203 | 7.5% |
| LABS, linear alkyl benzene sulfonate Biosoft S101 | 7.5 |
| Propylene Glycol | 3.75 |
| Sodium citrate | 3.75 |
| Sodium Lauryl Sulfate | 3.75 |
| LAE10 | 1.25 |
| Lauric acid, sodium salt | 0.625 |
| Water | qs |
| Total surfactant | 20% |
| Final pH | 10 |
| Dose per load (to 0.06% surfactant) | 0.6 g/200 ml wash solution |

Two-inch stain swatches (Tenside stain Swissatest EMPA 125 (Lot 03-04), Testfabrics) were washed in water, diluted "Lab Liquid A" detergent or diluted detergent with added Branched C12 amine oxide (2,4-diethyl-N,N-dimethyloctan-1-amine oxide, Example 44). After washing and drying, the fabric brightness was measured with a Konica Minolta colorimeter. Treatments were performed on triplicate swatches in three independent treatments, and the brightness (L*) average and standard deviation were calculated for each treatment. The three treatments were statistically different from each other ($p<0.02$).

TABLE 16

| Treatment | Fabric brightness (L*) | | |
|---|---|---|---|
| | avg | stdev | group |
| No detergent | 55.17 | 0.40 | A |
| No additive | 60.31 | 1.1 | B |
| +3% Branched C12 amine oxide | 62.45 | 0.7 | C |

Example 53: Foaming of C12 Amine Oxide Added to a Commercial Laundry Liquid

The surface foam volume and foam persistence of solutions of the amine oxides with linear and branched hydrophobes from Examples 25 and 26 were compared. A commercial laundry liquid was diluted in deionized water according to the dosing instructions; 4.2 ml/L Persil Original. The diluted detergent was supplemented with 0%, 2%, 5% (based on wt laundry liquid) of LAO or Branched C12 AO,(2,4-diethyl-N,N-dimethyloctan-1-amine oxide, Example 66), and the solutions mixed briefly and used immediately. 250 ml of each test solution was added the beaker of a Waring blender, capped, and then blended on High for 30 seconds and immediately transferred to a 1 L graduated cylinder. The total volume of foam plus liquid, as well as the liquid layer alone was recorded. The foam and liquid volumes were recorded again after 5 minutes. All tests were performed in triplicate. The average foam volume only (excluding the liquid volume) is reported in the Table 17 below.

TABLE 17

| Sample | Initial foam volume (ml) | Foam volume After 5 min (ml) | Difference |
|---|---|---|---|
| Persil Original | 553 | 327 | 226 |
| Persil 2% LAO | 527 | 473 | 54 |
| Persil 5% LAO | 513 | 507 | 6 |
| Persil 2% oxoC12 | 560 | 303 | 257 |
| Persil 5% oxoC12 | 560 | 280 | 280 |
| Persil 5% oxoC12 | 810 | 530 | 280 |

Example 54: Branched C12 Amine Oxide Pre-Treater on Lipstick Stain

Different surfactants (6%) were incorporated into a simple Pre-Treater formula:
Standard Pre-Treater (PT) Formula
6% surfactant
6% propylene glycol
2% trisodium citrate
2% poly(acrylic acid), sodium salt, MW 5,000

Standardized stain swatches (Lipstick on polyester/cotton fabric, CFT PCS-216, Lot 110) were cut into 2-inch squares, and 0.2 ml of the Standard PT formula was applied to the center of each swatch. After 5 minutes, the swatches were washed in cold water (20 C) in a benchtop vessel in diluted Tide, rinsed and air dried. Treatments were performed in triplicate. The fabric brightness after washing is reported as (L*) and the change in the color of the swatches after treatment, washing and drying as delta E, with higher values representing better stain removal.

TABLE 18

| | Lipstick | |
|---|---|---|
| | L* | deltaE |
| No pre-treatment | 74.2 | 10.9 |
| Surfactant in PT Formula (6%) | | |
| LAE10 | 77.9 | 18.2 |
| APG | 78.0 | 18.9 |
| LABS | 78.4 | 19.4 |
| Branched C12 amine oxide (2,4-diethyl-N,N-dimethyloctan-1-amine oxide, Example 44) | 80.2 | 23.3 |

Example 55: Stain Removal of Branched C12 Amine Oxide in a Stain Remover with Hydrogen Peroxide A stain remover was formulated with surfactants and hydrogen peroxide.
Hydrogen Peroxide Pre-Treater (PT) Formula
3% hydrogen peroxide
3% amine oxide
1% linear alkylbenzene sulfonate
Adjust to pH 9 with NaOH Standardized stain swatches (beef fat on poly/cotton, CFT-PC-61; Lot 004) were cut into 1-inch squares, accurately weighed and treated in triplicate with 0.1 ml of the Hydrogen Peroxide Pre-treater formula containing either a linear or branched amine oxide. After 5 minutes, the swatches were washed in 200 ml diluted Tide for 30 minutes, rinsed in 200 ml de-ionized water for 30 minutes, then air-dried overnight. The % weight lost after pre-treatment, washing and drying (a measure of oily soil removal) is reported in the Table 21 below.

TABLE 19

| Amine oxide in Hydrogen Peroxide Pre-treater formula (3%) | % wt loss |
|---|---|
| Lauramine oxide (LAO) | 9.7 |
| Branched C12 amine oxide (2,4-diethyl-N,N-dimethyloctan-1-amine oxide, Example 44) | 13.4 |

Example 56: Stain Removal of Linear and Branched Amine Oxides Added to a Commercial Pre-Treater A commercial stain remover pre-treater spray was used as the base formulation. The commercial pre-treater spray (Zout) contains Water; C14-15 pareth-7; C12-15 pareth-3; Boric acid; Calcium chloride; Sodium hydroxide; Propylene glycol; Sodium chloride; Protease, lipase, amylase; Dimethicone; Methylisothiazolone and Fragrance.

Standardized stain swatches (beef fat on poly/cotton, CFT-PC-61; Lot 004) were cut into 1-inch squares, accurately weighed and treated in triplicate with 0.1 ml of a commercial pre-treater formula, or with the commercial pre-treater Zout or with Zout supplemented with 3 wt % lauramine oxide or 3 wt % Branched C12 amine oxide, 2,4-diethyl-N,N-dimethyloctan-1-amine oxide. After 5 minutes, the swatches were washed in 200 ml diluted Tide for 30 minutes, rinsed in 200 ml de-ionized water for 30 minutes, then air-dried overnight. The % weight lost after pre-treatment, washing and drying (a measure of oily soil removal) is reported in the Table 20 below.

TABLE 20

| | % wt loss | | |
|---|---|---|---|
| Additive in Zout (3%) | Trial 1 | Trial 2 | Avg |
| No additive in Pre-treater | 0.31 | 0.41 | 0.36 |
| Lauramine oxide | 7.5 | 6.3 | 6.9 |
| Branched C12 amine oxide (2,4-diethyl-N,N-dimethyloctan-1-amine oxide, Example 44) | 11.0 | 8.8 | 9.9 |

Example 57: ASTM 4265 Stain Removal in Cold Water (Branched C12 AO Added to Commercial Pre-Treater)

The stain-removal activities of a commercial stain pre-treater with and without the addition of 3 wt % branched C12 amine oxide were compared in a washing machine test for stain removal in cold water. ASTM 4265 is a Standard Guide for Evaluating Stain Removal Performance in Home Laundering.

A commercial stain remover pre-treater spray was used as the base formulation. The commercial pre-treater spray (Zout) contains Water; C14-15 pareth-7; C12-15 pareth-3; Boric acid; Calcium chloride; Sodium hydroxide; Propylene glycol; Sodium chloride; Protease, lipase, amylase; Dimethicone; Methylisothiazolone and Fragrance.

The base formulation was tested alone or augmented with 3 wt % branched C12 amine oxide. The pre-treater (0.3 ml) was applied to the center of each stain on a stain panel and allowed to sit for 5 minutes before washing in liquid laundry detergent. The stain panel was the standard SwissaTest EMPA 102; a pre-soiled Cotton-Jersey (23×19 cm) with 15 different stains (3 cm), available from TestFabrics, Inc., West Pittston Pa. The test laundry formulations were evaluated in separate loads in a household front-loading high-efficiency (HE) washing machine connected to a city water source. The cold water wash option was selected on the machine. The water temperature was monitored using an in-wash recording device, and stayed between 15 and 20 C for the duration of the test period. Each load contained a pre-stained fabric swatch and clean ballast fabric. The manufacturer-recommended laundry liquid dose was used for each detergent.

The relative degree of stain removal is assessed instrumentally. The stain removal index (SRI) is calculated for each stain type, and the average and total SRI across all 15 stains is reported. A higher SRI indicates better stain removal.

TABLE 21

| Detergent for post-wash | No Pre-treater | Commercial pre-treater | Commercial Pre-treater + 3% Branched C12 amine oxide (2,4-diethyl-N,N-dimethyloctan-1-amine oxide, Example 45) |
|---|---|---|---|
| | Average SRI | | |
| Tide | 34 | 40 | 47 |
| Persil | 31 | 40 | 45 |
| All Free Clear | 30 | 42 | 46 |
| | Total SRI | | |
| Tide | 511 | 594 | 701 |
| Persil | 467 | 600 | 678 |
| All Free Clear | 447 | 634 | 691 |

In the specification, there have been disclosed certain embodiments of the invention and, although specific terms are employed, they are used in a generic and descriptive sense only and not for purposes of limitation, the scope of the invention being set forth in the following claims.

We claim:

1. A trialkylamine oxide having the formula:

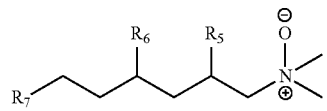

wherein R5, and R7 are independently at least one of C₃H₇, C₂H₅, CH₃, or H, or mixtures thereof; and wherein R6 is independently C₃H₇, C₂H₅, or CH₃ or mixtures thereof.

2. A trialkylamine oxide having the formula:

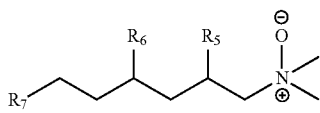

wherein R5 and R6 are C₃H₇, C₂H₅, CH₃, or mixtures thereof; and wherein R7 is one of C₃H₇, C₂H₅, CH₃, H or mixtures thereof.

3. The trialkylamine oxide of claim 2 wherein R6 is C₂H₅.

4. The trialkylamine oxide of claim 2 wherein R5 and R6 independently are C₂H₅.

5. The trialkylamine oxide of claim 4 which is 2,4-diethyl-N,N-dimethyloctan-1-amine oxide.

6. The trialkylamine oxide of claim 1 wherein R5 is CH₃.

7. The trialkylamine oxide of claim 6 wherein R5 is CH₃ and R6 is C₂H₅.

8. The trialkylamine oxide of claim 7 which is 4-ethyl-N,N-2-trimethyloctan-1-amine oxide.

9. A composition comprising at least one trialkylamine oxide of claim 1.

10. The composition of claim 9 comprising at least one nonionic surfactant, anionic surfactant, cationic surfactant, amphoteric surfactant, or mixtures thereof.

11. The composition of claim 9 comprising 0.01% to 30% by weight of said trialkylamine oxide based on the total weight of the composition equaling 100 weight %.

12. The composition of claim 9 comprising at least one bleach compound, hydrogen peroxide compound, or mixtures thereof.

13. The composition of claim 9 used in home care products, industrial cleaners, agrochemical formulations, coatings, fuel treatments, oil cleaners, oil recovery, oil dispersants, disinfectants, water treatments, bleaches, detergents, stain removers, soaps, oily soil cleaners, grease cutters, soft surface cleaners or hard surface cleaners.

14. The composition of claim 9 comprising dish detergents, kitchen surface cleaners, bathroom surface cleaners, upholstery cleaners, laundry stain removers, carpet cleaners, carpet spot removers, or laundry detergents.

* * * * *